(12) United States Patent
Stith et al.

(10) Patent No.: US 12,268,469 B2
(45) Date of Patent: Apr. 8, 2025

(54) MEDICAL IMAGING SYSTEMS AND METHODS THAT FACILITATE USE OF DIFFERENT FLUORESCENCE IMAGING AGENTS

(71) Applicant: Intuitive Surgical Operations, Inc., Sunnyvale, CA (US)

(72) Inventors: Curtis W. Stith, Santa Cruz, CA (US); Jeffrey M. DiCarlo, Austin, TX (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 606 days.

(21) Appl. No.: 17/296,180

(22) PCT Filed: Nov. 26, 2019

(86) PCT No.: PCT/US2019/063178
§ 371 (c)(1),
(2) Date: May 21, 2021

(87) PCT Pub. No.: WO2020/112724
PCT Pub. Date: Jun. 4, 2020

(65) Prior Publication Data
US 2022/0007942 A1 Jan. 13, 2022

Related U.S. Application Data

(60) Provisional application No. 62/774,023, filed on Nov. 30, 2018.

(51) Int. Cl.
*A61B 5/00* (2006.01)
*A61B 1/06* (2006.01)
(Continued)

(52) U.S. Cl.
CPC .......... *A61B 5/0071* (2013.01); *A61B 1/0655* (2022.02); *A61B 90/30* (2016.02); *A61B 1/00009* (2013.01)

(58) Field of Classification Search
None
See application file for complete search history.

(56) References Cited

U.S. PATENT DOCUMENTS

2004/0186351 A1* 9/2004 Imaizumi ............. A61B 1/0646
 600/476
2006/0052710 A1* 3/2006 Miura ................. A61B 1/0646
 600/476

(Continued)

FOREIGN PATENT DOCUMENTS

CN 107072520 A 8/2017
CN 107920726 A 4/2018
(Continued)

OTHER PUBLICATIONS

International Search Report and Written Opinion for Application No. PCT/US2019/063178 mailed on Feb. 20, 2020, 10 pages.
(Continued)

*Primary Examiner* — Katherine L Fernandez

(57) ABSTRACT

An exemplary medical imaging system includes a visible light illumination system configured to selectively emit one of a first visible light biased to a first wavelength and a second visible light biased to a second wavelength, a fluorescence excitation illumination system configured to selectively emit one of a first fluorescence excitation illumination having a third wavelength and a second fluorescence excitation illumination having a fourth wavelength, and an illumination source control unit configured to selectively direct the visible light illumination system to emit the second visible light and the fluorescence excitation illumination system to emit the first fluorescence excitation illumination for use with a first fluorescence imaging agent, and selectively direct the visible light illumination system to emit the first visible light and the fluorescence excitation illumination system to emit the second fluorescence excita- (Continued)

tion illumination for use with a second fluorescence imaging agent.

13 Claims, 15 Drawing Sheets

(51) Int. Cl.
*A61B 90/30* (2016.01)
*A61B 1/00* (2006.01)

(56) References Cited

U.S. PATENT DOCUMENTS

| | | | | |
|---|---|---|---|---|
| 2008/0249368 | A1* | 10/2008 | Takei | A61B 1/0655 600/181 |
| 2009/0236541 | A1 | 9/2009 | Lomnes et al. | |
| 2010/0094136 | A1* | 4/2010 | Nakaoka | A61B 1/05 600/178 |
| 2012/0004508 | A1 | 1/2012 | McDowall et al. | |
| 2017/0209050 | A1* | 7/2017 | Fengler | G01J 3/4406 |
| 2019/0029090 | A1* | 1/2019 | Ikehara | A61B 90/30 |
| 2019/0110686 | A1* | 4/2019 | Kato | A61B 5/0071 |
| 2019/0209061 | A1* | 7/2019 | Katra | A61B 5/1455 |
| 2021/0137369 | A1* | 5/2021 | Meester | G02B 5/208 |

FOREIGN PATENT DOCUMENTS

| | | |
|---|---|---|
| WO | WO-2016032729 A1 | 3/2016 |
| WO | WO-2017164101 A1 | 9/2017 |
| WO | WO-2018008062 A1 | 1/2018 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2019/063178, mailed on Jun. 10, 2021, 8 pages.

* cited by examiner

MEDICAL IMAGING SYSTEMS AND METHODS THAT FACILITATE USE OF DIFFERENT FLUORESCENCE IMAGING AGENTS

RELATED APPLICATIONS

The present application is a U.S. National Stage Application under 35 U.S.C. § 371 of International Application No. PCT/US2019/063178, filed on Nov. 26, 2019, which claims priority to U.S. Provisional Patent Application No. 62/774,023, filed on Nov. 30, 2018, the contents of which are hereby incorporated by reference in their entirety.

BACKGROUND INFORMATION

Some medical imaging systems are configured to capture fluorescence images of a surgical area within a patient while the patient undergoes a surgical procedure. The fluorescence images allow medical personnel (e.g., a surgeon) to readily identify cellular activity or structures (e.g., blood vasculature) within the surgical area during the surgical procedure.

To facilitate fluorescence imaging, a fluorescence imaging agent may be introduced (e.g., injected) into a bloodstream or other anatomical feature of the patient. The fluorescence imaging agent includes any suitable dye, protein, or other substance that emits fluorescence illumination when exposed to fluorescence excitation illumination generated by a fluorescence excitation illumination source included in a medical imaging system. The medical imaging system may capture the fluorescence illumination and render a fluorescence image based on the captured fluorescence illumination.

Different fluorescence imaging agents require different wavelengths of fluorescence excitation illumination. For example, a first exemplary fluorescence imaging agent will only fluoresce when excited by fluorescence excitation illumination that has a wavelength of around 405 nanometers ("nm"), while a second exemplary fluorescence imaging agent will only fluoresce when excited by fluorescence excitation illumination that has a wavelength of around 650 nm.

SUMMARY

An exemplary medical imaging system comprises a visible light illumination system configured to selectively emit one of a first visible light biased to a first wavelength associated with a first color, and a second visible light biased to a second wavelength associated with a second color; a fluorescence excitation illumination system configured to selectively emit one of a first fluorescence excitation illumination having a third wavelength to elicit fluorescence illumination by a first fluorescence imaging agent, the third wavelength closer to the first wavelength than to the second wavelength, and a second fluorescence excitation illumination having a fourth wavelength to elicit fluorescence illumination by a second fluorescence imaging agent, the fourth wavelength closer to the second wavelength than to the first wavelength; and an illumination source control unit communicatively coupled to the visible light illumination system and the fluorescence excitation illumination system, the illumination source control unit configured to selectively direct the visible light illumination system to emit the second visible light and the fluorescence excitation illumination system to emit the first fluorescence excitation illumination for use with the first fluorescence imaging agent, and selectively direct the visible light illumination system to emit the first visible light and the fluorescence excitation illumination system to emit the second fluorescence excitation illumination for use with the second fluorescence imaging agent.

Another exemplary medical imaging system comprises a visible light illumination system configured to selectively emit one of a first visible light biased to a first wavelength associated with a first color, and a second visible light biased to a second wavelength associated with a second color; a fluorescence excitation illumination system configured to selectively emit one of a first fluorescence excitation illumination having a third wavelength to elicit fluorescence illumination by a first fluorescence imaging agent, the third wavelength closer to the first wavelength than to the second wavelength, and a second fluorescence excitation illumination having a fourth wavelength to elicit fluorescence illumination by a second fluorescence imaging agent, the fourth wavelength closer to the second wavelength than to the first wavelength; a pixel-level broadband infrared cutoff filter that covers the second pixel and that is configured to prevent the second pixel from collecting infrared light; and a narrowband cutoff filter that covers the first, third, and fourth pixels and that is configured to prevent the first, third, and fourth pixels from collecting at least one of the first fluorescence excitation illumination and the second fluorescence excitation illumination.

Another exemplary medical imaging system comprises a visible light illumination system configured to selectively emit one of a blue-biased visible light, and a red-biased visible light; a fluorescence excitation illumination system configured to selectively emit one of a first fluorescence excitation illumination configured to elicit fluorescence illumination by a first fluorescence imaging agent, the first fluorescence excitation illumination comprising visible light in a blue color region of a visible light range, and a second fluorescence excitation illumination configured to elicit fluorescence illumination by a second fluorescence imaging agent, the second fluorescence excitation illumination comprising infrared light; and an illumination source control unit communicatively coupled to the visible light illumination system and the fluorescence excitation illumination system, the illumination source control unit configured to identify a fluorescence imaging agent used in a patient, determine that the fluorescence imaging agent is the first fluorescence imaging agent, and selectively direct, in response to the determination that the fluorescence imaging agent is the first fluorescence imaging agent, the visible light illumination system to emit the second visible light and the fluorescence excitation illumination system to emit the first fluorescence excitation illumination for use with the first fluorescence imaging agent.

An exemplary illumination source control unit comprises a memory storing instructions; a processor communicatively coupled to the memory, a visible light illumination system configured to selectively emit one of a first visible light biased to a first wavelength associated with a first color, and a second visible light biased to a second wavelength associated with a second color; and a fluorescence excitation illumination system configured to selectively emit one of a first fluorescence excitation illumination having a third wavelength to elicit fluorescence illumination by a first fluorescence imaging agent, the third wavelength closer to the first wavelength than to the second wavelength, and a second fluorescence excitation illumination having a fourth wavelength to elicit fluorescence illumination by a second fluorescence imaging agent, the fourth wavelength closer to the second wavelength than to the first wavelength; the processor configured to execute the instructions to selectively direct the visible light illumination system to emit the second visible light and the fluorescence excitation illumination system to emit the first fluorescence excitation illumination for use with the first fluorescence imaging agent, and selectively direct the visible light illumination system to emit the first visible light and the fluorescence excitation illumination system to emit the second fluorescence excitation illumination for use with the second fluorescence imaging agent.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
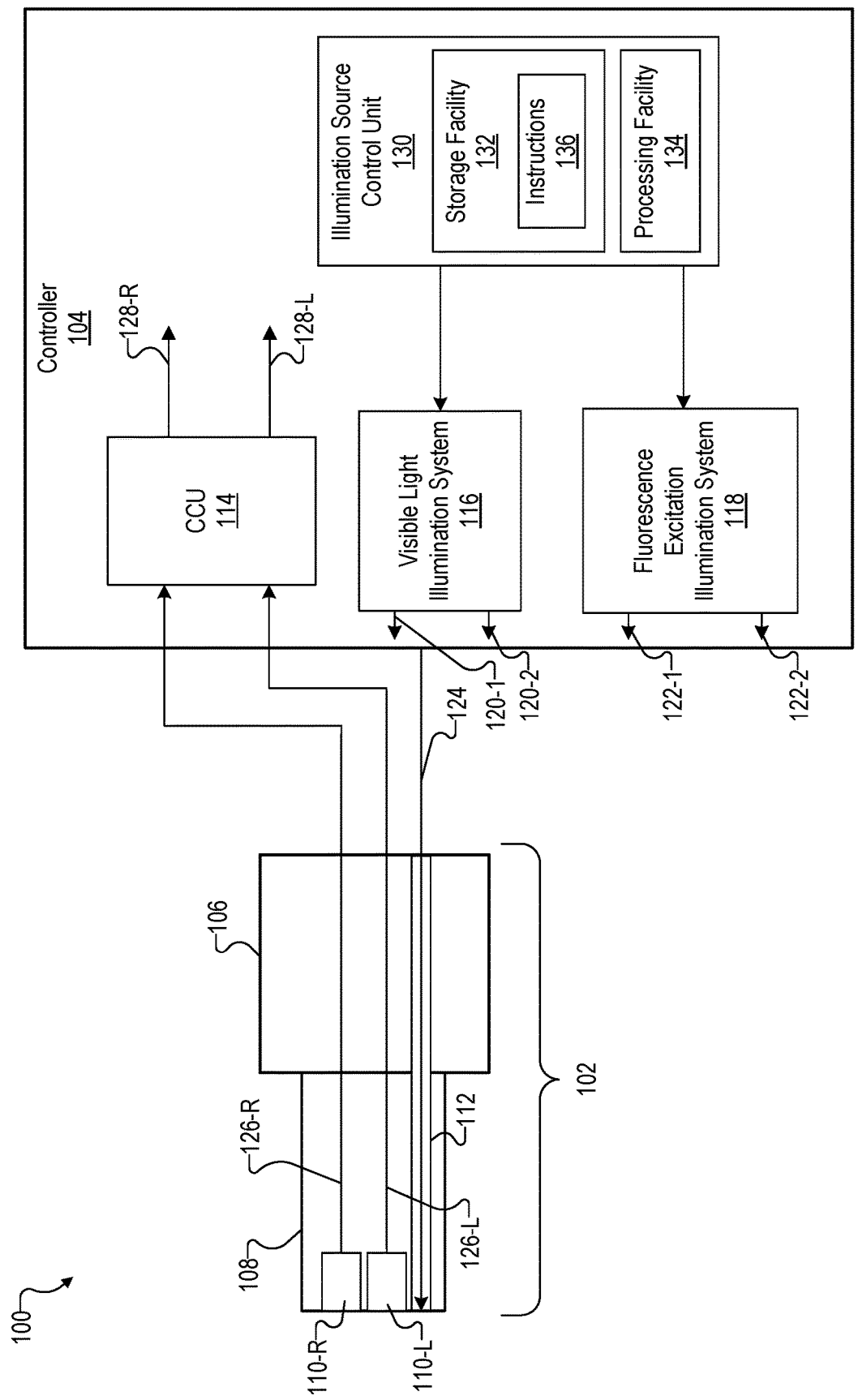
FIG. 1 illustrates an exemplary medical imaging system according to principles described herein.

Medical imaging systems and methods that facilitate use of different fluorescence imaging agents are described herein. As will be described in more detail below, an exemplary medical imaging system used to image a surgical area of a patient includes a visible light illumination system and a fluorescence excitation illumination system. The visible light illumination system is configured to selectively emit one of a first visible light biased to a first wavelength associated with a first color and a second visible light biased to a second wavelength associated with a second color. The fluorescence excitation illumination system is configured to selectively emit one of a first fluorescence excitation illumination configured to elicit fluorescence illumination by a first fluorescence imaging agent and a second fluorescence excitation illumination configured to elicit fluorescence illumination by a second fluorescence imaging agent. The first fluorescence excitation illumination has a wavelength closer to the first wavelength than to the second wavelength. The second fluorescence excitation illumination has a wavelength closer to the second wavelength than to the first wavelength.

In this configuration, an illumination source control unit communicatively coupled to the visible light illumination system and the fluorescence excitation illumination system may selectively direct the visible light illumination system to emit the second visible light and the fluorescence excitation illumination system to emit the first fluorescence excitation illumination in situations where it is desired to use the first fluorescence imaging agent. Likewise, the illumination source control unit may selectively direct the visible light illumination system to emit the first visible light and the fluorescence excitation illumination system to emit the second fluorescence excitation illumination where it is desired to use the second fluorescence imaging agent.

For example, the illumination source control unit may receive user input that identifies a fluorescence imaging agent used in a patient, determine that the fluorescence imaging agent is the first fluorescence imaging agent, and direct, in response to the determination that the fluorescence imaging agent is the first fluorescence imaging agent, the visible light illumination system to emit the second visible light and the fluorescence excitation illumination system to emit the first fluorescence excitation illumination. Alternatively, the illumination source control unit may receive user input that identifies a fluorescence imaging agent used in a patient, determine that the fluorescence imaging agent is the second fluorescence imaging agent, and direct, in response to the determination that the fluorescence imaging agent is the second fluorescence imaging agent, the visible light illumination system to emit the first visible light and the fluorescence excitation illumination system to emit the second fluorescence excitation illumination where it is desired to use the second fluorescence imaging agent.

In some examples, the visible light illumination system is implemented by a first visible light illumination source configured to emit the first visible light and a second visible light illumination source configured to emit the second visible light. Alternatively, the visible light illumination system may be implemented by a single adjustable visible light illumination source that may be adjusted to emit either the first visible light or the second visible light.

Likewise, the fluorescence excitation illumination system may be implemented by a first fluorescence excitation illumination source configured to emit the first fluorescence excitation illumination and a second fluorescence excitation illumination source configured to emit the second fluorescence excitation illumination. Alternatively, the fluorescence excitation illumination system may be implemented by a single adjustable fluorescence excitation illumination source that may be adjusted to emit either the first fluorescence excitation illumination or the second fluorescence excitation illumination.

The following example assumes that the visible light illumination system is implemented by first and second visible light illumination sources and that the fluorescence excitation illumination system is implemented by first and second fluorescence excitation illumination sources.

In this example, the first visible light illumination source may be configured to emit blue-biased visible light (i.e., visible light that has more of a blue component than green or red components), and the second visible light illumination source may be configured to emit red-biased visible light (i.e., visible light that has more of a red component than green or blue components). The first fluorescence excitation illumination source is configured to emit fluorescence excitation illumination having a wavelength around 405 nm, which is relatively close to a blue color region of the visible light range. The second fluorescence excitation illumination source is configured to emit fluorescence excitation illumination having a wavelength around 650 nm, which is closer to a red color region of the visible light range than to the blue color region of the visible light range.

Continuing with this illustration, when it is desired to use a fluorescence imaging agent that fluoresces in response to the fluorescence excitation illumination having a wavelength at or near 405 nm (which is near the blue color region), the illumination source control unit may selectively activate the first fluorescence excitation illumination source and the second visible light illumination source (i.e., the visible light illumination source configured to emit red-biased visible light). The illumination source control unit may also deactivate the second fluorescence excitation illumination source and the first visible light illumination source (or ensure that they remain deactivated). As will be described in more detail below, this configuration may ensure that the visible light is not unduly filtered out by a narrowband cutoff filter used to filter out the fluorescence excitation illumination. This, in turn, may result in higher quality (e.g., sharper) color and fluorescence images.

When it is desired to use a fluorescence imaging agent that fluoresces in response to the fluorescence excitation illumination having a wavelength at or near 650 nm (which is near the red color region), the illumination source control unit may selectively activate the second fluorescence excitation illumination source and the first visible light illumination source (i.e., the visible light illumination source configured to emit blue-biased visible light). The illumination source control unit may also deactivate the first fluorescence excitation illumination source and the second visible light illumination source (or ensure that they remain deactivated). As will be described in more detail below, this configuration may ensure that the visible light is not unduly filtered out by a narrowband cutoff filter used to filter out the fluorescence excitation illumination. This, in turn, may result in higher quality (e.g., sharper) color and fluorescence images.

These and other advantages and benefits of the systems and methods described herein will be made apparent herein. Moreover, additional advantages, benefits, and details related to the systems and methods described herein are described in co-pending U.S. Provisional Patent Application No. 62/774,041, filed the same day as the present application and entitled "MEDICAL IMAGING SYSTEMS AND METHODS," the contents of which are incorporated herein by reference in their entirety.

FIG. 1 illustrates an exemplary medical imaging system 100 configured to capture images of a scene. In some examples, the scene may include a surgical area associated with a patient. The surgical area may, in certain examples, be entirely disposed within the patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments used to perform the surgical procedure are located. In other examples, a surgical area may be at least partially disposed external to the patient.

As shown, medical imaging system 100 includes an imaging device 102 and a controller 104. Medical imaging system 100 may include additional or alternative components as may serve a particular implementation. For example, medical imaging system 100 may include various optical and/or electrical signal transmission components (e.g., wires, lenses, optical fibers, choke circuits, waveguides, etc.), a cable that houses electrical wires and/or optical fibers and that is configured to interconnect imaging device 102 and controller 104, etc.

Imaging device 102 may be implemented by an endoscope or other camera device configured to capture images of a scene. As shown, imaging device 102 includes a camera head 106, a shaft 108 coupled to and extending away from camera head 106, image sensors 110 (i.e., a right-side image sensor 110-R and a left-side image sensor 110-L) at a distal end of shaft 108, and an illumination channel 112. In the example of FIG. 1, imaging device 102 is stereoscopic. Alternatively, in other examples imaging device 102 may be monoscopic (e.g., by including one image sensor 110 instead of two image sensors 110).

Imaging device 102 may be manually handled and controlled (e.g., by a surgeon performing a surgical procedure on a patient). Alternatively, camera head 106 may be coupled to a manipulator arm of a computer-assisted surgical system, an example of which will be provided below. In this configuration, imaging device 102 may be controlled using robotic and/or teleoperation technology.

The distal end of shaft 108 may be positioned at or near a scene that is to be imaged by imaging device 108. For example, the distal end of shaft 108 may be inserted into a patient. In this configuration, imaging device 102 may be used to capture images of anatomy and/or other objects within the patient.

Image sensors 110 may each be implemented by any suitable image sensor, such as a charge coupled device ("CCD") image sensor, a complementary metal-oxide semiconductor ("CMOS") image sensor, or the like. In some examples, as shown in FIG. 1, image sensors 110 are positioned at the distal end of shaft 108. Alternatively, image sensors 110 may be positioned closer to a proximal end of shaft 108, inside camera head 106, or outside imaging device 102 (e.g., inside controller 104). In these alternative configurations, optics (e.g., lenses, optical fibers, etc.) included in shaft 108 and/or camera head 106 may convey light from a scene to image sensors 110.

Image sensors 110 are configured to detect (e.g., capture, collect, sense, or otherwise acquire) light. For example, image sensor 110-R is configured to detect the light from a right-side perspective, and image sensor 110-L is configured to detect the light from a left-side perspective. In the example of FIG. 1, the light detected by image sensors 110 includes visible light that reflects off of an object located within a scene. However, as will be described herein, image sensors 110 may additionally or alternatively detect infrared fluorescence illumination emitted by a fluorescence imaging agent located within the scene. As will be illustrated below, image sensors 110 may convert the detected light into data representative of one or more images. Exemplary implementations of image sensors 110 are described herein.

Illumination channel 112 may be implemented by one or more optical components (e.g., optical fibers, light guides, lenses, etc.). As will be described below, illumination may be provided by way of illumination channel 112 to illuminate a scene.

Controller 104 may be implemented by any suitable combination of hardware and software configured to control and/or interface with imaging device 102. For example, controller 104 may be at least partially implemented by a computing device included in a computer-assisted surgical system.

Controller 104 includes a camera control unit ("CCU") 114, a visible light illumination system 116, and a fluorescence excitation illumination system 118. In some examples, CCU 114 and/or illumination systems 116 and 118 are alternatively included in imaging device 102 (e.g., in camera head 106).

CCU 114 is configured to control various parameters (e.g., activation times, auto exposure, etc.) of image sensors 110. As will be described below, CCU 114 may be further configured to receive and process image data from image sensors 110. While CCU 114 is shown in FIG. 1 to be a single unit, CCU 114 may alternatively be implemented by a first CCU configured to control right-side image sensor 110-R and a second CCU configured to control left-side image sensor 110-L.

Visible light illumination system 116 is configured to selectively generate and emit visible light that is selectively biased to one of a plurality of wavelengths (i.e., colors). For example, visible light illumination system 116 may be configured to selectively generate and emit visible light 120-1 and visible light 120-2.

Visible light 120-1 and 120-2 may each include one or more color components. For example, visible light 120-1 and 120-2 may each include white light that includes a full spectrum of color components (e.g., red, green, and blue color components). The red color component has wavelengths between approximately 635 and 700 nm. The green color component has wavelengths between approximately 520 and 560 nm. The blue color component has wavelengths between approximately 450 and 490 nm.

Visible light 120-1 and 120-2 are each biased to include more of one color component than another color component. For example, visible light 120-1 is biased to a first wavelength associated with a first color such that visible light 120-1 includes more of the first color than second and third colors. Likewise, visible light 120-2 is biased to a second wavelength associated with a second color such that visible light 120-2 includes more of the second color than the first and third colors. In the examples provided herein, visible light 120-1 is blue-biased (i.e., biased to include more blue than green or red) and visible light 120-2 is red-biased (i.e., biased to include more red than green or blue).

While visible light illumination system 116 is shown in FIG. 1 as selectively generating and emitting two differently biased visible light 120, visible light illumination system 116 may selectively generate and emit any number of differently biased visible light. For example, visible light illumination system 116 may be further configured to generate and emit visible light that is green-biased (i.e., biased to include more green than red or blue).

Fluorescence excitation illumination system 118 is configured to selectively generate and emit differently biased fluorescence excitation illumination. For example, fluorescence excitation illumination system 118 may selectively generate and emit fluorescence excitation illumination 122-1 or fluorescence excitation illumination 122-2.

Fluorescence excitation illumination 122-1 and 122-2 have different wavelengths. As such, fluorescence excitation illumination 122-1 and 122-2 are configured to elicit fluorescence illumination by different fluorescence imaging agents. For example, fluorescence excitation illumination 122-1 may have a wavelength such that fluorescence excitation illumination 122-1 elicits fluorescence illumination by a first fluorescence imaging agent (and not a second fluorescence imaging agent). In contrast, fluorescence excitation illumination 122-2 may have a wavelength such that fluorescence excitation illumination 122-2 elicits fluorescence illumination by the second fluorescence imaging agent (and not the first fluorescence imaging agent). The elicited fluorescence illumination may be detected by any of the image sensors described herein and used to generate fluorescence images that indicate various cellular activity or structures (e.g., blood vasculature in real-time).

In some examples, at least one of fluorescence excitation illumination 122-1 and 122-2 include infrared light. In other words, at least one of fluorescence excitation illumination 122-1 and 122-2 has a wavelength in an infrared light region. The infrared light region includes wavelengths from around 700 nm (the edge of the red visible light region) to around one millimeter. More particularly, at least one of fluorescence excitation illumination 122-1 and 122-2 may have a wavelength included in the near-infrared light region, which is in the infrared light region and includes wavelengths from about 700 nm to about 950 nm. For example, one of fluorescence excitation illumination 122-1 and 122-2 may have a wavelength of around 803 nm. As another example, one of fluorescence excitation illumination 122-1 and 122-2 may have a wavelength of around 785 nm.

In some examples, at least one of fluorescence excitation illumination 122-1 and 122-2 include visible light. For example, one of fluorescence excitation illumination 122-1 and 122-2 may have a wavelength of around 405 nm, which is near the blue color region of the visible light range. As another example, one of fluorescence excitation illumination 122-1 and 122-2 may have a wavelength of around 650 nm, which is near the red color region of the visible light range.

While fluorescence excitation illumination system 118 is shown in FIG. 1 to emit two differently biased fluorescence excitation illuminations 122, fluorescence excitation illumination system 118 may emit any number of differently biased fluorescence excitation illuminations. For example, fluorescence excitation illumination system 118 may be configured to generate and output either infrared or visible light.

Visible light illumination system 116 and fluorescence excitation illumination system 118 may each be implemented by any suitable combination of hardware and software.

For example, visible light illumination system 116 may be implemented by a first visible light illumination source configured to emit visible light 120-1 and a second visible light illumination source separate from the first visible light illumination source and configured to emit visible light 120-2. Alternatively, visible light illumination system 116 may be implemented by a single adjustable visible light illumination source that may be adjusted to emit either visible light 120-1 or visible light 102-2. Such adjustment may be performed in any suitable manner.

Likewise, fluorescence excitation illumination system 118 may be implemented by a first fluorescence excitation illumination source configured to emit fluorescence excitation illumination 122-1 and a second fluorescence excitation illumination source configured to emit fluorescence excitation illumination 122-2. Alternatively, fluorescence excitation illumination system 118 may be implemented by a single adjustable fluorescence excitation illumination source that may be adjusted to emit either fluorescence excitation illumination 122-1 or fluorescence excitation illumination 122-2. Such adjustment may be performed in any suitable manner.

Visible light 120 and fluorescence excitation illumination 122 may be conveyed as illumination 124 that traveled by way of illumination channel 112 to a distal end of shaft 108, where illumination 124 exits to illuminate a scene. Hence, illumination 124 may include any combination of visible light 120 and fluorescence excitation illumination 122 as may serve a particular implementation.

To capture one or more images of a scene, visible light illumination system 116 and/or fluorescence excitation illumination system 118 may be directed to emit illumination 124, which travels via illumination channel 112 to the scene. In cases where illumination 124 includes visible light, image sensors 110 detect illumination 124 reflected from one or more surfaces in the scene. In cases where illumination 124 includes fluorescence excitation illumination, image sensors 110 may additionally or alternatively detect fluorescence illumination that is elicited by the fluorescence excitation illumination.

Image sensors 110 (and/or other circuitry included in imaging device 102) may convert the detected illumination into image data 124 representative of one or more images of the scene. For example, image sensor 110-R outputs image data 124-R representative of images captured from a right-side perspective and image sensor 110-L outputs image data 124-L representative of images captured from a left-side perspective. Image data 124 may have any suitable format.

Image data 124 is transmitted from image sensors 110 to CCU 114. Image data 124 may be transmitted by way of any suitable communication link between image sensors 110 and CCU 114. For example, image data 124 may be transmitted by way of wires included in a cable that interconnects imaging device 102 and controller 104.

CCU 114 may process (e.g., packetize and/or format) image data 124 and output processed image data 128 (e.g., processed image data 128-R corresponding to image data 124-R and processed image data 128-L corresponding to image data 124-L). Processed image data 128 may be transmitted to an image processing system, which may prepare processed image data 128 for display on one or more display devices (e.g., in the form of video content and/or one or more still images). For example, the image processing system may, based on image data 128, generate one or more color (e.g., full-color and/or grayscale) images and/or one or more fluorescence images (e.g., color and/or grayscale fluorescence images) for display on one or more display devices.

Medical imaging system 100 may be used to capture fluorescence images generated using different fluorescence imaging agents. To this end, an illumination source control unit 130 ("control unit 130") may be communicatively coupled to visible light illumination system 116 and fluorescence excitation illumination system 118. As described herein, control unit 130 is configured to selectively control (e.g., activate and/or adjust) visible light illumination system 116 and/or fluorescence excitation illumination system 118. As shown, in the example of FIG. 1, control unit 130 is included in controller 104. In alternative embodiments, control unit 130 may be included in or implemented by a computing device in communication with controller 104.

As shown, control unit 130 may include, without limitation, a storage facility 132 and a processing facility 134 selectively and communicatively coupled to one another. Facilities 132 and 134 may each include or be implemented by hardware and/or software components (e.g., processors, memories, communication interfaces, instructions stored in memory for execution by the processors, etc.). For example, facilities 132 and 134 may be implemented by any component in a computer-assisted surgical system. In some examples, facilities 132 and 134 may be distributed between multiple devices and/or multiple locations as may serve a particular implementation.

Storage facility 132 may maintain (e.g., store) executable data used by processing facility 134 to perform any of the operations described herein. For example, storage facility 132 may store instructions 136 that may be executed by processing facility 134 to perform any of the operations described herein. Instructions 136 may be implemented by any suitable application, software, code, and/or other executable data instance. Storage facility 132 may also maintain any data received, generated, managed, used, and/or transmitted by processing facility 134.

Processing facility 134 may be configured to perform (e.g., execute instructions 136 stored in storage facility 132 to perform) various operations associated with controlling visible light illumination system 116 and fluorescence excitation illumination system 118. Examples of such operations will now be described. It will be recognized that operations described herein as being performed by control unit 130 are performed by processing facility 134 of control unit 130.

In the following examples, visible light 120-1 is biased to a first wavelength associated with a first color and visible light 120-2 is biased to a second wavelength associated with a second color. Furthermore, in the following examples, fluorescence excitation illumination 122-1 has a third wavelength to elicit fluorescence illumination by a first fluorescence imaging agent, and fluorescence excitation illumination 122-2 has a fourth wavelength to elicit fluorescence illumination by a second fluorescence imaging agent. The third wavelength is closer to the first wavelength than to the second wavelength. The fourth wavelength is closer to the second wavelength than to the first wavelength.

For example, the first wavelength may be in the blue color region and therefore associated with a blue color while the second wavelength may be in the red color region and therefore associated with a red color. The third wavelength may be around 405 nm, which is closer to the blue color region than the red color region. The fourth wavelength may be around 650, 785, or 803 nm, which are all closer to the red color region than to the blue color region. The third and fourth wavelengths may each be any other value as may serve a particular implementation.

Control unit 130 may identify a fluorescence imaging agent used in a patient.

This may be performed in any suitable manner. For example, control unit 130 may receive user input (e.g., by way of a user interface) identifying the fluorescence imaging agent and/or a wavelength of the fluorescence imaging agent. As another example, control unit 130 may, during an initialization procedure, selectively direct fluorescence excitation illumination system 118 to emit fluorescence excitation illumination 122-1 and/or 122-2 while the fluorescence imaging agent is in the patient. While a particular fluorescence excitation illumination 122 is being applied, control unit 130 may determine whether fluorescence illumination is detected. If fluorescence illumination is detected while a particular fluorescence excitation illumination is being emitted, control unit 130 may identify the fluorescence imaging agent by identifying a wavelength of the fluorescence illumination.

Control unit 130 may determine that the identified fluorescence imaging agent is either the first fluorescence imaging agent or the second fluorescence imaging agent. For example, control unit 130 may maintain a lookup table in storage facility 202 that associates one or more fluorescence imaging agents with each of the different types of fluorescence excitation illumination that may be emitted by fluorescence excitation illumination system 118. Control unit 130 may refer to the lookup table to determine that the identified fluorescence imaging agent is associated with a particular one of fluorescence excitation illuminations.

To illustrate, control unit 130 may determine that the fluorescence imaging agent used in the patient fluoresces at a wavelength that is within a predetermined distance from the third wavelength of fluorescence excitation illumination 122-1. In response, control unit 130 may determine that the fluorescence imaging agent is the first fluorescence imaging agent.

In response to this determination, control unit 130 may selectively direct visible light illumination system 116 to emit visible light 120-2 and fluorescence excitation illumination system 118 to emit fluorescence excitation illumination 122-1. This may be performed in any suitable manner.

For example, in implementations where visible light illumination system 116 is implemented by a first visible light illumination source configured to emit visible light 120-1 and a second visible light illumination source configured to emit visible light 120-2, control unit 130 may selectively direct visible light illumination system 116 to emit visible light 120-2 by selectively activating (e.g., turning on or otherwise enabling) the second visible light illumination source and ensuring that the first visible light illumination source is deactivated.

As another example, in implementations where visible light illumination system 116 is implemented by a single adjustable visible light illumination source, control unit 130 may selectively direct visible light illumination system 116 to emit visible light 120-2 by adjusting the single adjustable visible light illumination source to selectively visible light 120-2. This adjustment may be performed in any suitable manner, such as by adjusting a filtering of light output by the adjustable visible light illumination source.

Likewise, in implementations where fluorescence excitation illumination system 118 is implemented by a first fluorescence excitation illumination source configured to emit fluorescence excitation illumination 122-1 and a second fluorescence excitation illumination source configured to emit fluorescence excitation illumination 122-2, control unit 130 may selectively direct fluorescence excitation illumination system 118 to emit fluorescence excitation illumination 122-1 by selectively activating the first fluorescence excitation illumination source and ensuring that the second fluorescence excitation illumination source is deactivated.

As another example, in implementations where fluorescence excitation illumination system 118 is implemented by a single adjustable fluorescence excitation illumination source, control unit 130 may selectively direct fluorescence excitation illumination system 118 to emit fluorescence excitation illumination 122-1 by adjusting the single adjustable fluorescence excitation illumination source to emit fluorescence excitation illumination 122-1. This adjustment may be performed in any suitable manner, such as by adjusting a filtering of the illumination output by the adjustable visible light illumination source.

As will be made apparent herein, by control unit 130 selectively directing visible light illumination system 116 to emit visible light 120-2 and fluorescence excitation illumination system 118 to emit fluorescence excitation illumination 122-1, the systems and methods described herein may ensure that visible light 120-2 is not unduly filtered out by a narrowband cutoff filter used to filter out fluorescence excitation illumination 122-1. This, in turn, may result in higher quality (e.g., sharper) color and fluorescence images.

Moreover, this configuration may ensure that visible light 120-2 is does not overwhelm the fluorescence illumination emitted by the fluorescence imaging agent.

As another example, control unit 130 may determine that the fluorescence imaging agent used in the patient fluoresces at a wavelength that is within a predetermined distance from the fourth wavelength of fluorescence excitation illumination 122-2. In response, control unit 130 may determine that the fluorescence imaging agent is the second fluorescence imaging agent.

In response to this determination, control unit 130 may selectively direct visible light illumination system 116 to emit visible light 120-1 and fluorescence excitation illumination system 118 to emit fluorescence excitation illumination 122-2. This may be done in any of the ways described herein. In this state, control unit 130 may ensure that visible light illumination system does not emit visible light 120-2 and that fluorescence excitation illumination system 118 does not emit fluorescence excitation illumination 122-1. As will be made apparent herein, this configuration may ensure that visible light 120-1 is not unduly filtered out by a narrowband cutoff filter used to filter out fluorescence excitation illumination 122-2. This, in turn, may result in higher quality (e.g., sharper) color and fluorescence images.

To facilitate color and/or fluorescence imaging of a scene, various filters may be implemented within medical imaging system 100. Exemplary filter arrangements that may be used in accordance with the systems and methods described herein will now be described.

Figure 2:
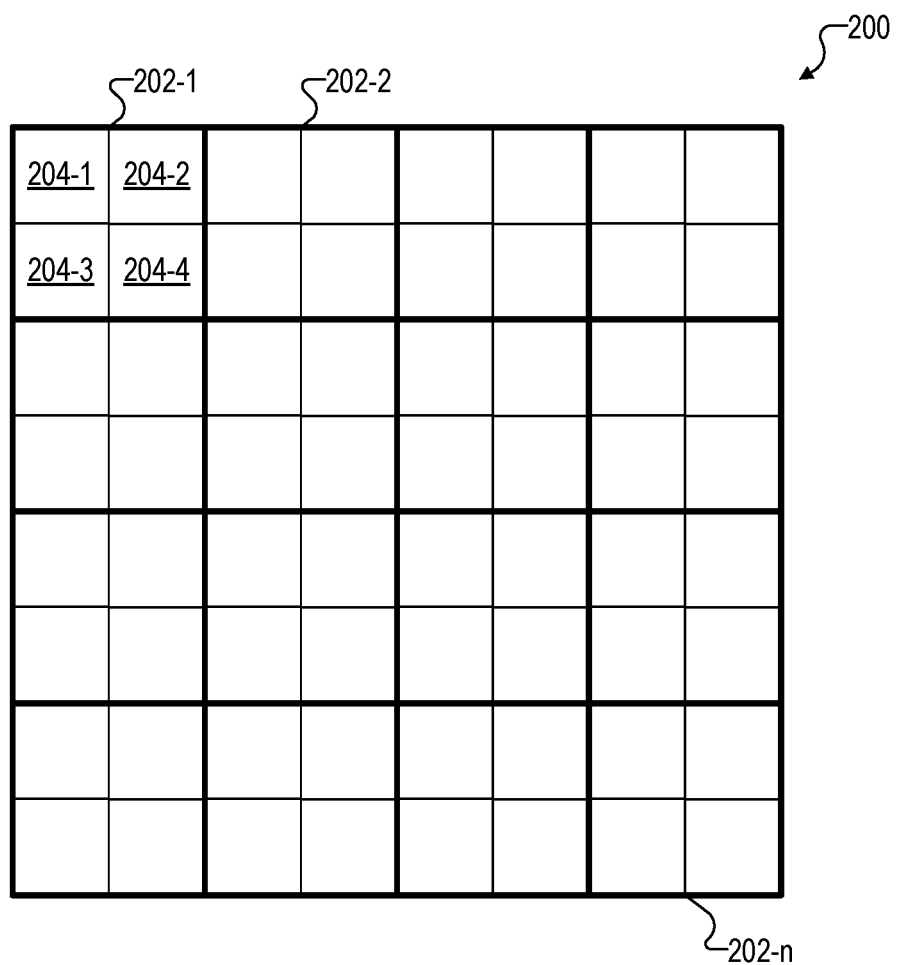
FIG. 2 shows an exemplary image sensor according to principles described herein.

FIG. 2 shows an exemplary image sensor 200. Image sensor 200 may implement image sensors 110 and/or any other image sensor included in an imaging device. As shown, image sensor 200 include a plurality of pixel arrays 202 (e.g., pixel array 202-1 through pixel array 202-*n*). Each pixel array 202 includes a two-by-two arrangement of pixels 204. For example, pixel array 202-1 includes a first pixel 204-1, a second pixel 204-2, a third pixel 204-3, and a fourth pixel 204-4 arranged as shown in FIG. 2. Image sensor 200 may include any suitable number of pixel arrays 202 as may serve a particular implementation.

To facilitate color imaging of a scene, image sensor 200 may include an arrangement of color filters that cover pixels 204. Each color filter is configured to allow its corresponding pixel 204 to detect only a particular color component of light incident on pixels 204. The color filters may cover pixels 204 by being coated on or otherwise adhered to a surface (e.g., a surface upon which light may be incident) of pixels 204. The color filters may alternatively cover pixels 204 in any other suitable manner.

In an exemplary color filter arrangement, a first color filter covers pixel 204-1, a second color filter covers pixels 204-2 and 204-3, and a third color filter covers pixel 204-4. The first color filter is configured to allow pixel 204-1 to collect a first visible light color component and prevent pixel 204-1 from collecting second and third visible light color components. The second color filter is configured to allow pixels 204-2 and 204-3 to each collect the second visible light color component and prevent pixels 204-2 and 204-3 from each collecting the first and third visible light color components. The third color filter is configured to allow pixel 204-4 to collect the third visible light color component and prevent pixel 204-4 from collecting the first and second visible light color components.

Figure 3A:
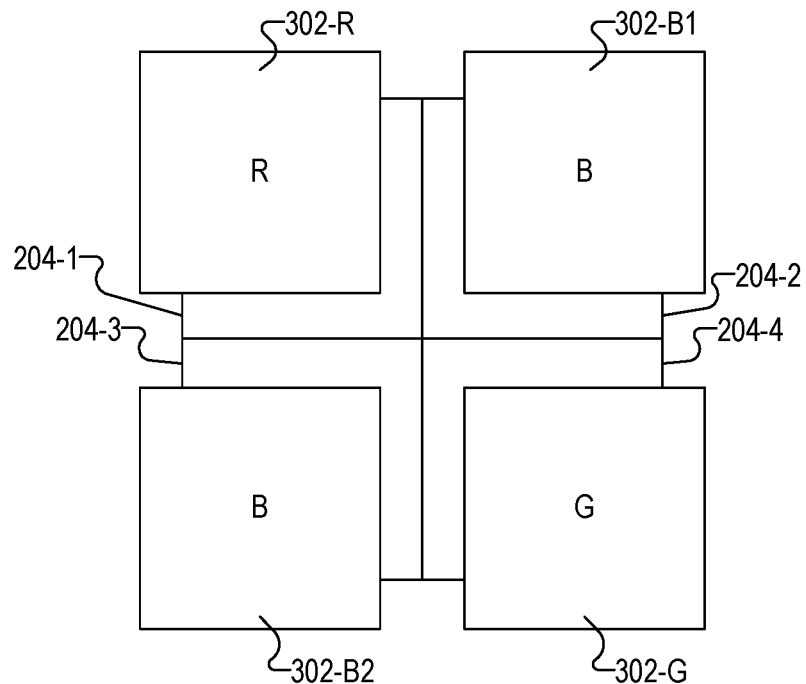
FIGS. 3A-4B show exemplary color filter arrangements according to principles described herein.
Figure 3B:
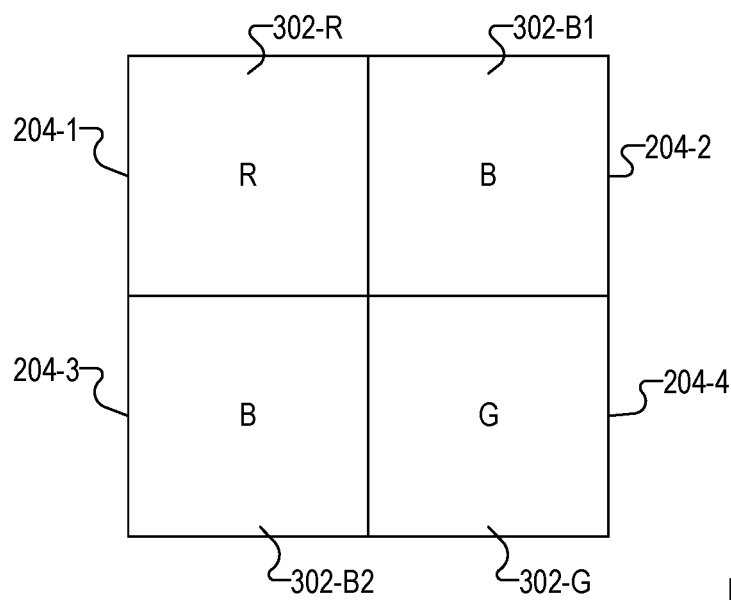

To illustrate, FIGS. 3A-3B show an exemplary color filter arrangement that covers pixels 204 and that may be used in accordance with the systems and methods described herein. As shown, a different color filter 302 may cover each pixel 204. For ease of illustration, FIG. 3A shows filters 302 slightly offset from pixels 204 while FIG. 3B shows filters 302 directly covering pixels 204.

As shown in FIGS. 3A-3B, a red filter 302-R covers pixel 204-1, a first blue filter 302-B1 covers pixel 204-2, a second blue filter 302-B2 covers pixel 204-3, and a green filter 302-G covers pixel 204-4. The filter arrangement shown in FIGS. 3A-3B is referred to herein as an RBBG because of the order in which the color filters 302 are arranged.

Red filter 302-R is configured to allow pixel 204-1 to collect a red component of visible light and prevent pixel 204-1 from collecting blue and green components of the visible light. Blue filters 302-B1 and 302-B2 are configured to allow pixels 204-2 and 204-3 to each collect the blue component of the visible light and prevent pixels 204-2 and 204-3 from each collecting the red and green components of the visible light. Green filter 302-G is configured to allow pixel 204-4 to collect the green component of the visible light and prevent pixel 204-4 from collecting the red and blue components of the visible light.

Other color filter arrangements that include two blue filters may also be used in accordance with the systems and methods described herein. For example, in an alternative embodiment, first blue filter 302-B1 may cover pixel 204-1, red filter 302-R may cover pixel 204-2, green filter 302-G may cover pixel 204-3, and second blue filter 302-B2 may cover pixel 204-4. This alternative filter arrangement may be referred to as BRBG.

By using a color filter arrangement that is fifty percent blue, such as that shown in FIGS. 3A-3B, the systems and methods described herein may more effectively capture blue-biased light used in medical imaging applications compared to conventional color filter arrangements that are only twenty-five percent blue. Therefore, a color filter arrangement that is fifty percent blue may produce sharper and more accurate images of a surgical area associated with a patient.

Figure 4A:
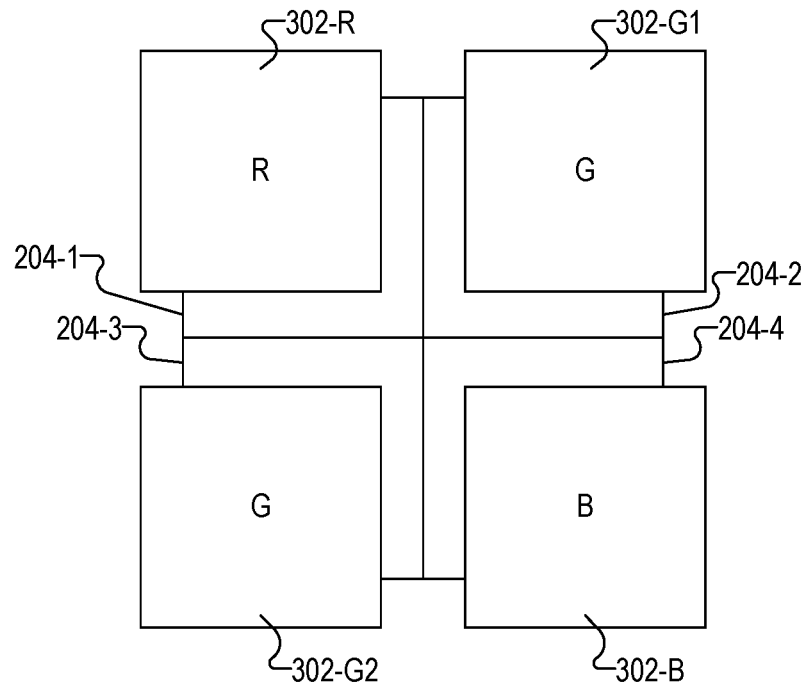
Figure 4B:
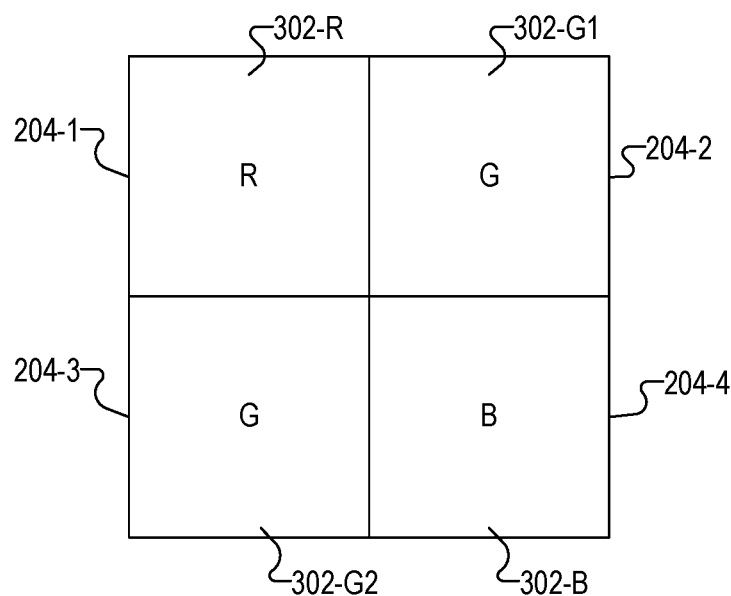

Other filter arrangements may alternatively be used in connection with the systems and methods described herein. For example, FIGS. 4A-4B show an exemplary RGGB color filter arrangement that covers pixels 204 and that may be used in accordance with the systems and methods described herein. For ease of illustration, FIG. 4A shows filters 302 slightly offset from pixels 204 while FIG. 4B shows filters 302 directly covering pixels 204.

As shown in FIGS. 4A-4B, red filter 302-R covers pixel 204-1, a first green filter 302-G1 covers pixel 204-2, a second green filter 302-G2 covers pixel 204-3, and a blue filter 302-B covers pixel 204-4. Red filter 302-R is configured to allow pixel 204-1 to collect a red component of visible light and prevent pixel 204-1 from collecting blue and green components of the visible light. Green filters 302-G1 and 302-G2 are configured to allow pixels 204-2 and 204-3 to each collect the green component of the visible light and prevent pixels 204-2 and 204-3 from each collecting the red and blue components of the visible light. Blue filter 302-B is configured to allow pixel 204-4 to collect the blue component of the visible light and prevent pixel 204-4 from collecting the red and green components of the visible light.

In some scenarios (e.g., when it is desired to generate a full-color or grayscale fluorescence image), visible light illumination system 116 and fluorescence excitation illumination system 118 concurrently emit visible light and fluorescence excitation illumination, respectively. In these scenarios, the pixels of image sensors 110 collect both visible light and fluorescence illumination without discriminating between the two types of illumination. Hence, image data 124 output by image sensors 110 includes data representative of both color components and a fluorescence illumination component (where the fluorescence illumination component may include either visible light or infrared light depending on the particular fluorescence excitation illumination that is provided).

Figure 5:
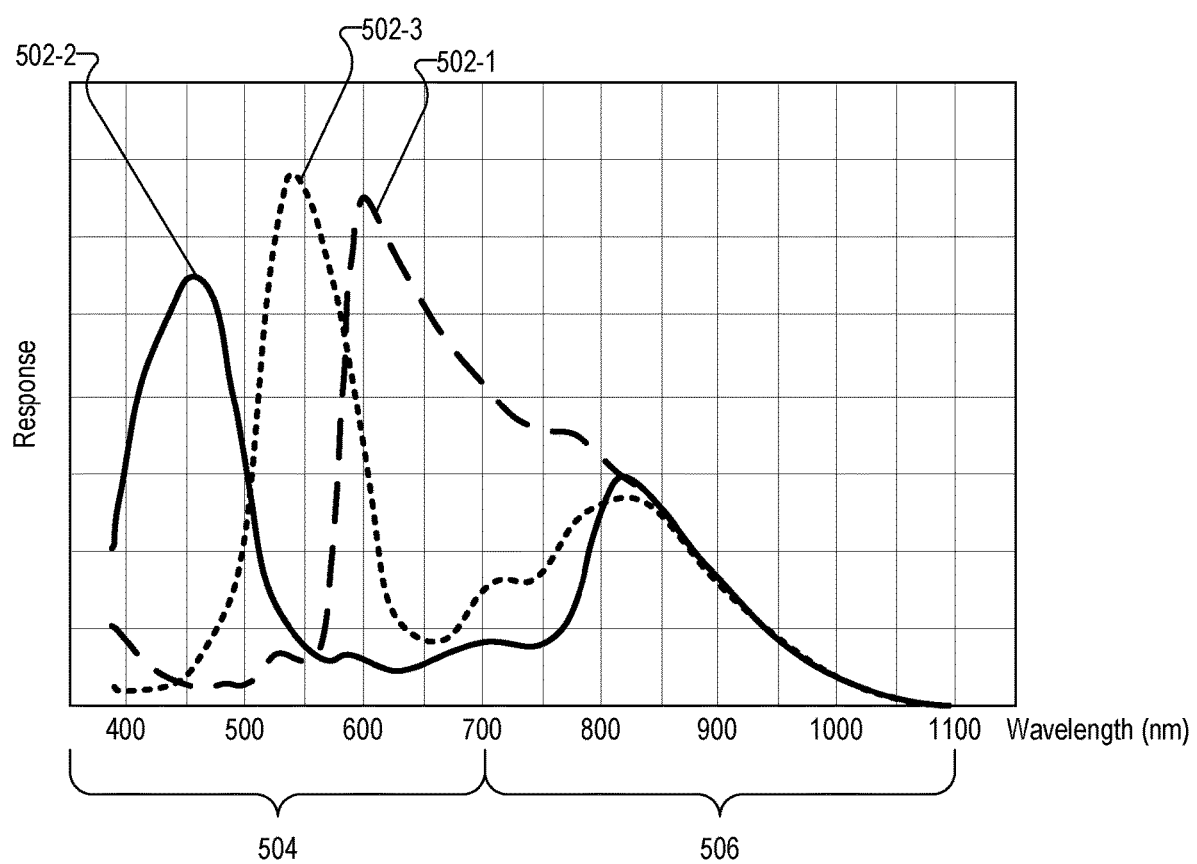
FIG. 5 shows spectral response curves for color filters according to principles described herein.

To illustrate, FIG. 5 shows spectral response curves 502 for color filters 302. For example, FIG. 5 shows a spectral response curve 502-1 for red filter 302-R, a spectral response curve 502-2 for blue filters 302-B1 and 302-B2, and a spectral response curve 502-3 for green filter 302-G. Spectral response curves 502 are represented by different variations of solid and dashed lines to visually distinguish spectral response curves 502 one from another. As shown, spectral response curves 502 are plotted along a horizontal axis that represents wavelengths included in a visible light range 504 and in an infrared light range 506.

Spectral response curves 502 show how each color filter 302 allows its corresponding pixel to collect a particular color component of visible light 120 while preventing the pixel from collecting other color components of visible light 120. For example, spectral response curve 502-1 has a relatively high response at wavelengths in the red color region of visible light range 504 and a relatively low response at wavelengths in other regions of visible light range 504. Hence, in the color filter arrangement shown in FIGS. 3A-3B, red filter 302-R allows pixel 204-1 to collect a red component of visible light 120 while preventing pixel 204-1 from collecting blue and green components of visible light 120. Spectral response curve 502-2 has a relatively high response at wavelengths in the blue color region of visible light range 504 and a relatively low response at wavelengths in other regions of visible light range 504. Hence, in the color filter arrangement shown in FIGS. 3A-3B, blue filters 302-B1 and 302-B2 allow pixels 204-2 and 204-3 to collect a blue component of visible light 120 while preventing pixels 204-2 and 204-3 from collecting red and green components of visible light 120. Spectral response curve 502-3 has a relatively high response at wavelengths in the green color region of visible light range 504 and a relatively low response at wavelengths in other regions of visible light range 504. Hence, in the color filter arrangement shown in FIGS. 3A-3B, green filter 302-G allows pixel 204-4 to collect a green component of visible light 120 while preventing pixel 204-4 from collecting red and blue components of visible light 120.

As also shown in FIG. 5, the spectral response curves 502 each have relatively high responses in infrared light range 506. In other words, each color filter 302 corresponding to spectral response curves 502 does not prevent pixels 204 from collecting at least some types of infrared light. To illustrate, as shown in FIG. 5, color filters 302 may not prevent pixels 204 from collecting near-infrared light.

Hence, one or more infrared cutoff filters covering one or more of pixels 204 may be included in medical imaging system 100 in configurations in which fluorescence excitation illumination system 118 is configured to emit infrared light. In these configurations, image data 128 includes color components and an infrared fluorescence illumination component (i.e., a component representative of fluorescence illumination 122 that has a wavelength in the infrared light range). The one or more infrared cutoff filters may allow an image processing system to distinguish between the color components and the infrared fluorescence illumination component included in image data 128. By distinguishing between the color components and the infrared fluorescence illumination component, the image processing system may be able to generate a color (e.g., full-color) fluorescence image.

Figure 6A:
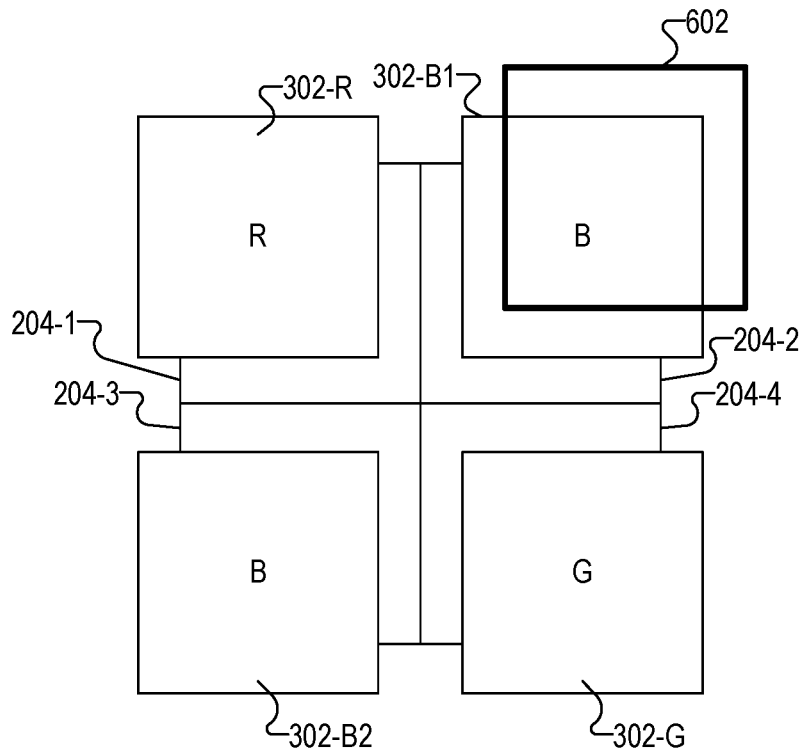
FIGS. 6A-6B illustrate a filter configuration according to principles described herein.
Figure 6B:
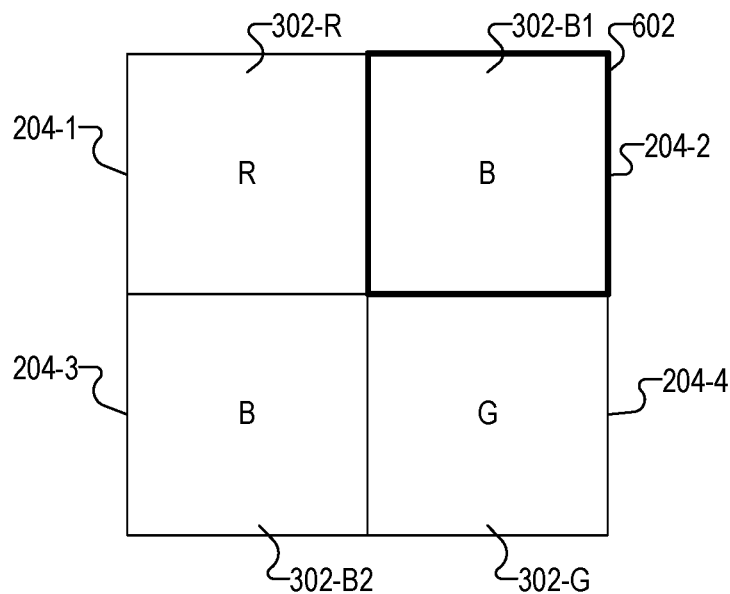

To illustrate, FIGS. 6A-6B are associated with the color filter arrangement shown in FIGS. 3A-3B and illustrate a filter configuration in which a pixel-level broadband infrared cutoff filter 602 ("cutoff filter 602") covers pixel 204-2. Cutoff filter 602 may be implemented by a coating that is configured to adhere to a surface of pixel 204-2 and/or in any other manner.

For ease of illustration, FIG. 6A shows filters 302 and 602 slightly offset from pixels 204 while FIG. 6B shows filters 302 and 602 directly covering pixels 204. Cutoff filter 602 is illustrated in FIGS. 6A-6B as being on top of blue color filter 302-61. However, in alternative embodiments, blue color filter 302-B1 may be on top of cutoff filter 602.

As shown, pixel-level broadband infrared cutoff filters similar to cutoff filter 602 do not cover pixels 204-1, 204-3, and 204-4. This may advantageously allow an image processing system to distinguish between the color components and the infrared fluorescence illumination component included in image data 128, as will be described below.

Figure 7:
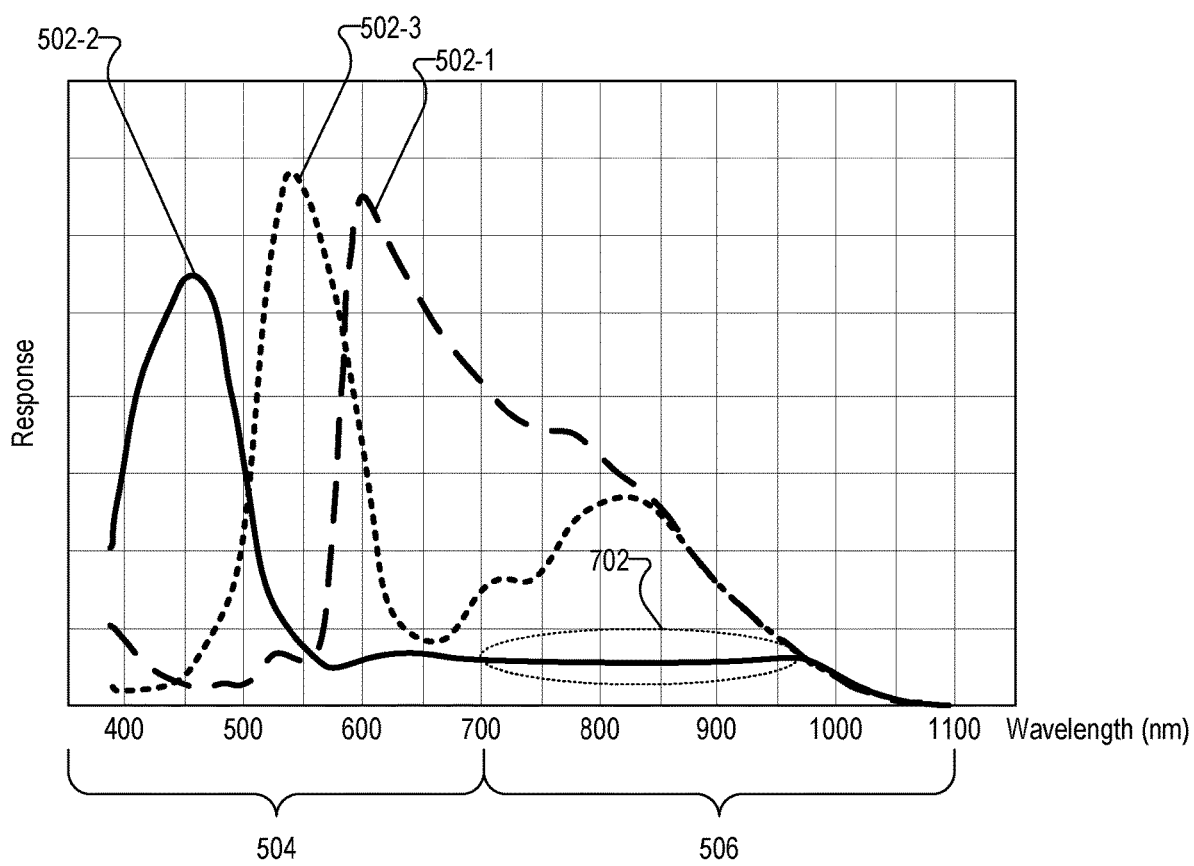
FIG. 7 shows spectral response curves for color filters according to principles described herein.

Cutoff filter 602 is configured to prevent pixel 204-2 from collecting infrared light having wavelengths included in relatively broad range of wavelengths (e.g., the entire near-infrared light range). This is illustrated in FIG. 7, which is similar to FIG. 5, except that in FIG. 7 the spectral response 502-2 of color filter 302-2 is relatively flat in the near-infrared light range (e.g., between 700 nm and 950 nm). This is highlighted in FIG. 7 by callout 702.

By preventing pixel 204-2 from collecting infrared light, cutoff filter 602 may effectively allow pixel 204-2 to collect only the blue component of visible light 120. In contrast, because pixel 204-3 is not covered by a cutoff filter similar to cutoff filter 602, pixel 204-3 collects both the blue component and the infrared fluorescence illumination elicited by fluorescence excitation illumination 122 when visible light illumination system 116 and fluorescence excitation illumination system 118 are concurrently emitting light. As will be described below, an image processing system may subtract a signal representative of the light collected by pixel 204-3 from a signal representative of the light collected by pixel 204-2 to identify an infrared fluorescence illumination component included in the signal representative of the light collected by pixel 204-2.

Figure 8A:
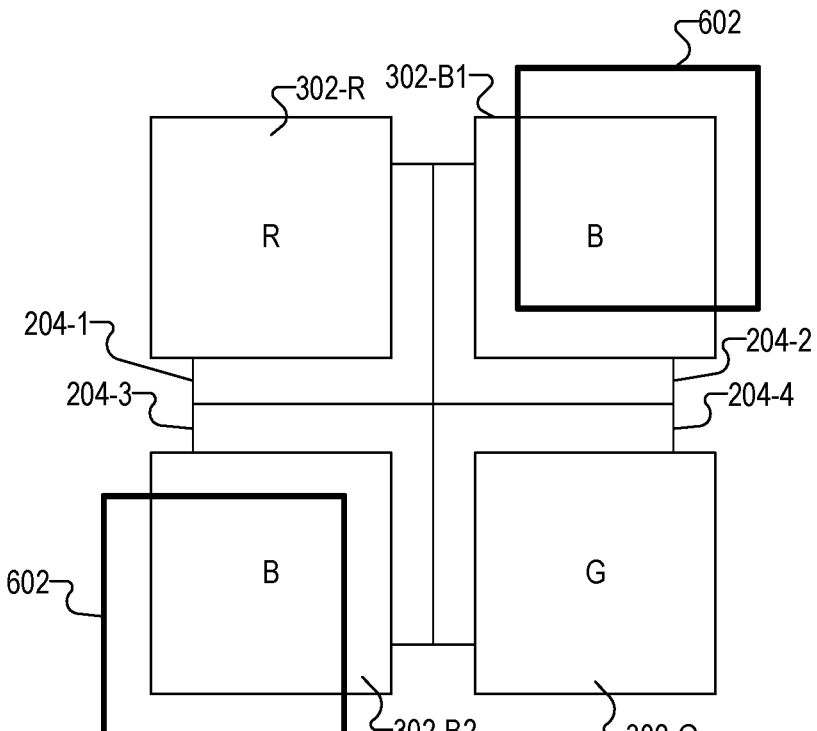
FIGS. 8A-10B illustrate exemplary filter configurations according to principles described herein.
Figure 8B:
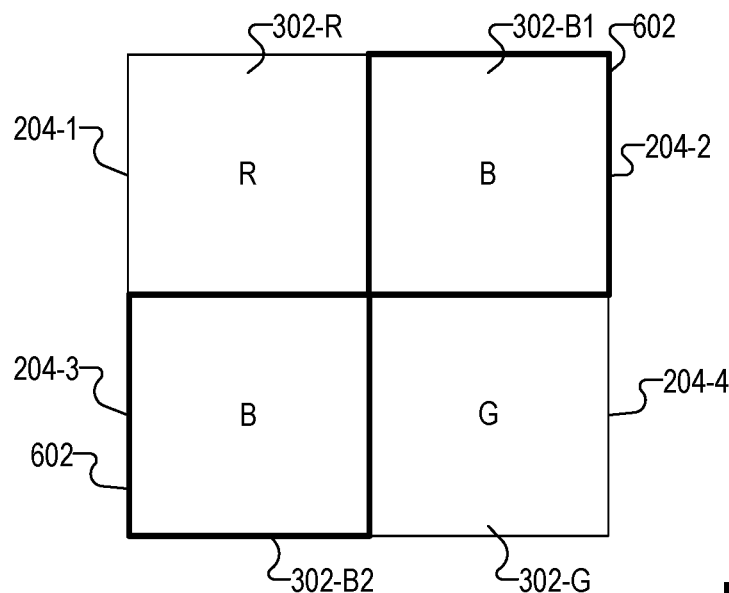

In some alternative embodiments, one or more of pixels 204-1, 204-3, and 204-4 may also be covered by a broadband infrared cutoff filter similar to cutoff filter 602. For example, FIGS. 8A-8B illustrate a filter configuration in which pixel-level broadband infrared cutoff filters 602 cover both pixels 204-2 and 204-3. For ease of illustration, FIG. 8A shows cutoff filters 602 slightly offset from pixels 204-2 and 204-3 while FIG. 8B shows filters 602 directly covering pixels 204-2 and 204-3. The filter configuration of FIGS. 8A-8B may increase the sharpness of color images and grayscale fluorescence images generated based on the light captured by pixels 204.

Figure 9A:
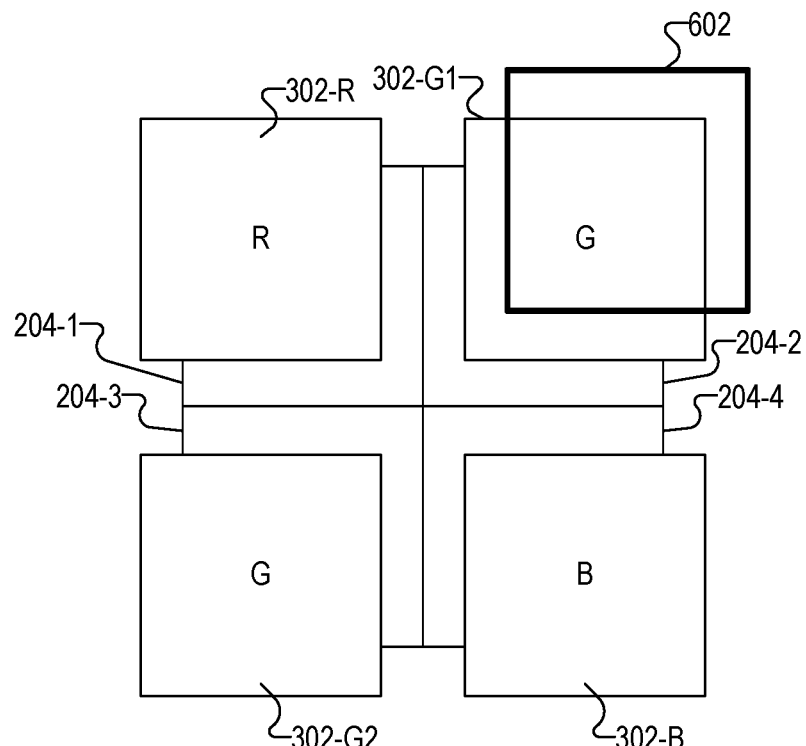
Figure 9B:
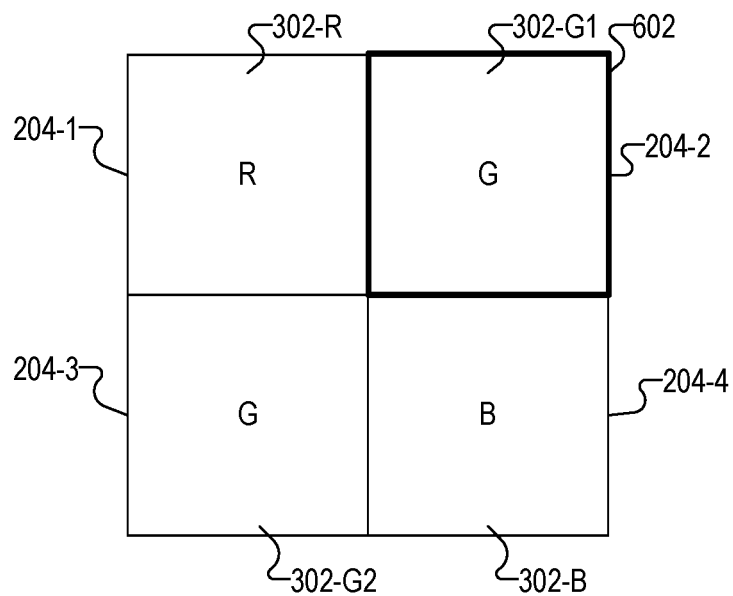

FIGS. 9A-9B show an alternative configuration in which cutoff filter 602 is used in conjunction with an RGGB filter configuration, such as the RGGB filter configuration illustrated in FIGS. 4A-4B. As shown, cutoff filter 602 covers pixel 204-2 without similar cutoff filters covering the remaining pixels 204-1, 204-3, and 204-4. For ease of illustration, FIG. 9A shows filters 302 and cutoff filter 602 slightly offset from pixels 204 while FIG. 9B shows filters 302 and cutoff filter 602 directly covering pixels 204. The configuration shown in FIGS. 9A-9B may be used, for example, in imaging applications (e.g., non-medical applications) where the visible light used as illumination is green-biased.

As mentioned, a fluorescence imaging agent may fluoresce at a different wavelength than fluorescence excitation illumination 402. For example, as mentioned above, an exemplary fluorescence imaging agent fluoresces at 830 nm when excited by fluorescence excitation illumination that has a wavelength of 803 nm. Because it is desirable to prevent pixels 204 from detecting fluorescence excitation illumination 122 while at the same time allowing at least some of pixels 204 to detect the fluorescence illumination emitted by a fluorescence imaging agent, a narrowband cutoff filter may be further included in the medical imaging systems described herein.

Figure 10A:
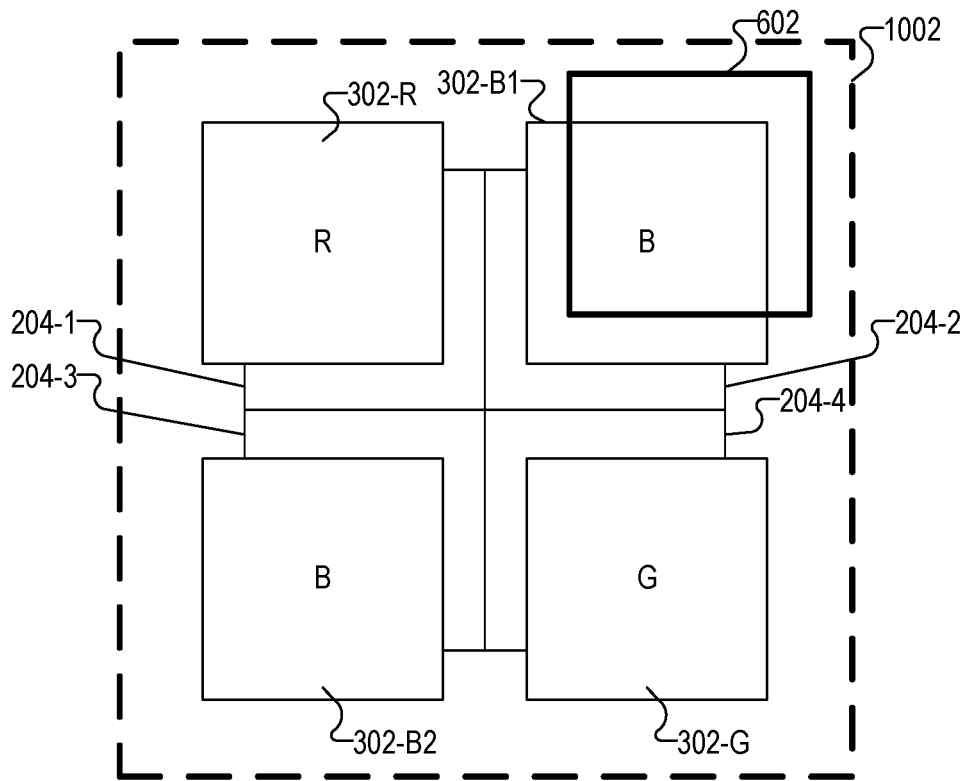

To illustrate, FIG. 10A show an exemplary filter configuration in which a narrowband cutoff filter 1002 covers all of pixels 204. Narrowband cutoff filter 1002 may be implemented as a glass filter, for example, that covers all of pixels 204 and that is on top of color filters 302 and cutoff filter 602. Narrowband cutoff filter 1002 is configured to prevent pixels 204 from collecting light having a wavelength included in a relatively narrow range of wavelengths (e.g., a range of 20 nm or less) that includes the wavelength of fluorescence excitation illumination 122. As such, narrowband cutoff filter 1002 effectively prevents pixels 204 from detecting fluorescence excitation illumination 122.

In some examples, narrowband cutoff filter 1002 is configured to prevent pixels 204 from collecting multiple different possible wavelengths (e.g., any combination of 405, 650, 785 and 803 nm) of fluorescence excitation illumination 122 that may be selectively emitted by fluorescence excitation illumination system 118. For example, narrowband cutoff filter 1002 may be implemented as a single glass filter that filters out all of these wavelengths. Alternatively, narrowband cutoff filter 1002 may be implemented as a layer of different glass filters each configured to filter out one of these wavelengths.

Figure 10B:
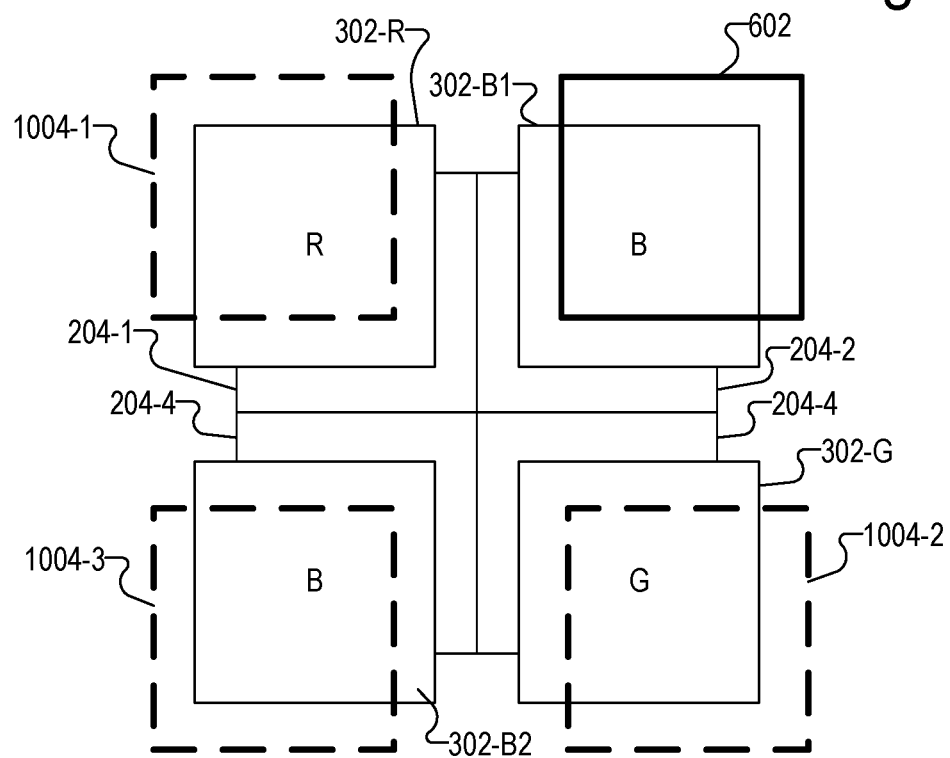

FIG. 10B shows an alternative configuration associated with the color filter arrangement of FIGS. 3A-3B in which pixel-level narrowband cutoff filters 1004-1, 1004-2, and 1004-3 cover pixels 204-1, 204-3, and 204-4, respectively. Pixel-level narrowband cutoff filters 1004 may be implemented in any suitable manner. Like narrowband cutoff filter 1002, pixel-level narrowband cutoff filters 1004 may effectively prevent pixels 204-1, 204-3, and 204-4 from detecting fluorescence excitation illumination 122. It will be recognized that in case where fluorescence excitation illumination 122 is infrared light, cutoff filter 602 likewise prevents pixel 204-2 from detecting fluorescence excitation illumination 122.

In some examples, multiple layers of narrowband cutoff filters 1002 may cover a particular pixel 204, where each layer is configured to filter out a different fluorescence illumination wavelength. For example, if fluorescence excitation illumination system 118 is configured to selectively emit fluorescence excitation illumination 122 having wavelengths of either 405 or 803 nm, two layers of pixel-level narrowband cutoff filters 1004-1, 1004-2, and 1004-3 cover pixels 204-1, 204-3, and 204-4, respectively. The first layer may be configured to filter out visible light having a wavelength of 405 nm, and the second layer may be configured to filter out infrared light having a wavelength of 803 nm.

Figure 11:
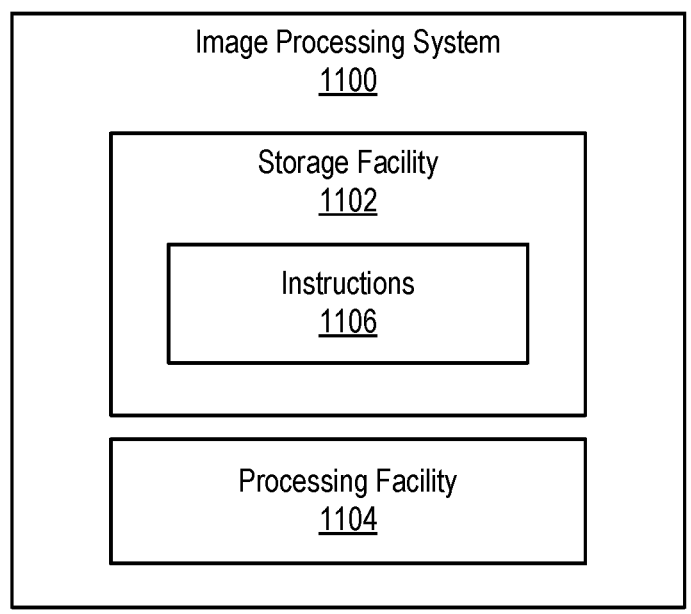
FIG. 11 illustrates an image processing system according to principles described herein.

FIG. 11 illustrates an image processing system 1100 that may be configured to generate, based on signals representative of light collected by pixels 204, one or more images for display on a display device. Image processing system 1100 may be included in or connected to any of the medical imaging systems described herein. For example, in some examples, image processing system 1100 is communicatively coupled to controller 104. In this configuration, image processing system 1100 may receive processed image data 128 as an input.

As shown, system 1100 may include, without limitation, a storage facility 1102 and a processing facility 1104 selectively and communicatively coupled to one another. Facilities 1102 and 1104 may each include or be implemented by hardware and/or software components (e.g., processors, memories, communication interfaces, instructions stored in memory for execution by the processors, etc.). For example, facilities 1102 and 1104 may be implemented by any component in a computer-assisted surgical system. In some examples, facilities 1102 and 1104 may be distributed between multiple devices and/or multiple locations as may serve a particular implementation.

Storage facility 1102 may maintain (e.g., store) executable data used by processing facility 1104 to perform any of the operations described herein. For example, storage facility 1102 may store instructions 1106 that may be executed by processing facility 1104 to perform any of the operations described herein. Instructions 1106 may be implemented by any suitable application, software, code, and/or other executable data instance. Storage facility 1102 may also maintain any data received, generated, managed, used, and/or transmitted by processing facility 1104.

Processing facility 1104 may be configured to perform (e.g., execute instructions 1106 stored in storage facility 1102 to perform) various operations associated with generating images for display on a display device.

For example, while visible light 120 and fluorescence excitation illumination 122 are being concurrently emitted (or, alternatively, after visible light 120 and fluorescence excitation illumination 122 have been emitted), processing facility 1104 may receive a first signal $S_1$ representative of light collected by pixel 204-1, a second signal $S_2$ representative of light collected by pixel 204-2, a third signal $S_3$ representative of light collected by pixel 204-3, and a fourth signal $S_4$ representative of light collected by pixel 204-4.

In this example, pixels 204 are covered by the filter arrangement shown in FIG. 10A or FIG. 10B (i.e., an RBBG color filter arrangement with cutoff filter 602 covering pixel 204-2 and narrowband cutoff filter 1002 or narrowband cutoff filters 1004 covering the remaining pixels 204-1, 204-3, and 204-4). It will also be assumed for purposes of this example that the fluorescence excitation illumination 122 has a wavelength in the infrared light range (e.g., 803 nm).

Hence, the signals received by processing facility 1104 may be represented by the following equations:

$$S_1 = R + FI$$

$$S_2 = B$$

$$S_3 = B + FI$$

$$S_4 = G + FI$$

In these equations, R represents the red component of the light captured by pixel 204-1, B represents the blue component of the light captured by pixels 204-2 and 204-3, G represents the green component of the light captured by pixel 204-4, and FI represents the infrared fluorescence illumination captured by pixels 204-1, 204-3, and 204-4. Note that none of the signals $S_1$ through $S_4$ includes the fluorescence excitation illumination 122 due to the presence of cutoff filter 602 covering pixel 204-2 and narrowband cutoff filter 1002 or narrowband cutoff filters 1004 covering the pixels 204-1, 204-3, and 204-4.

Figure 12:
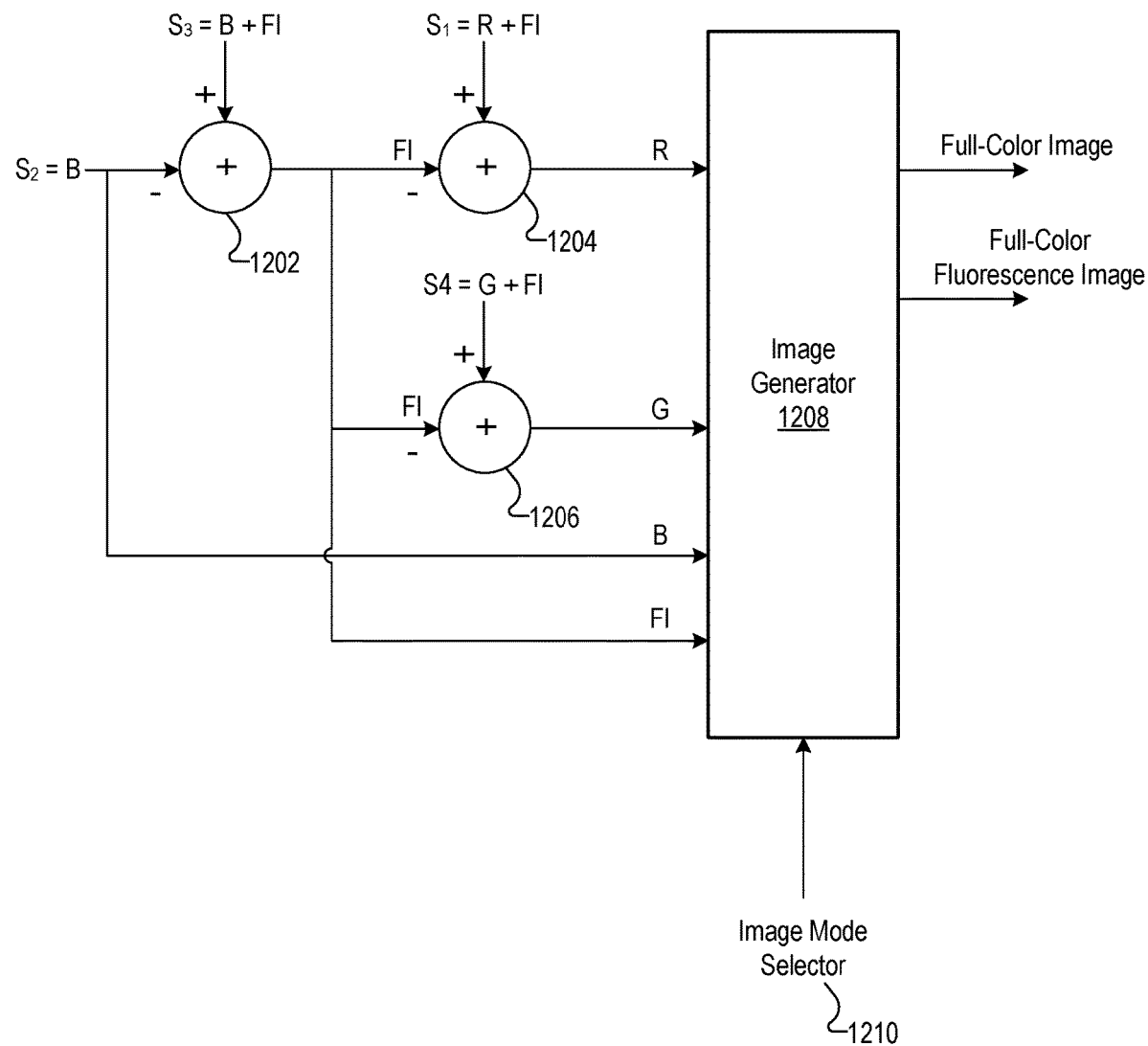
FIG. 12 shows various operations that may be performed by an imaging processing system to selectively generate a full-color image and a full-color fluorescence image according to principles described herein.

Processing facility 1104 may process signals $S_1$ through $S_4$ to selectively generate a full-color image (without fluorescence) and a full-color fluorescence image. For example, FIG. 12 shows various operations that may be performed by processing facility 1104 to selectively generate a full-color image and a full-color fluorescence image.

At summing block 1202, processing facility 1104 first subtracts $S_2$ from $S_3$ to identify an infrared fluorescence illumination component FI included in $S_3$. This subtraction may be performed using any suitable signal processing operation.

To identify the red component R and the green component G, processing facility 1104 subtracts FI from $S_1$ at summing block 1204 and FI from $S_4$ at summing block 1206. As shown, the output of summing block 1204 is a processed first signal representative of only the red component R and the output of summing block 1206 is a processed fourth signal representative of only the green component G.

As shown, R, G, B, and FI are all input into an image generator 1208, which may be implemented by processing facility 1104 in any suitable manner. Image generator 1208 may generate, based on a received image mode selector command 1210, various types of images for display by a display device. Image mode selector command 1210 may be provided by a user (e.g., a surgeon), by any component included in a computer-assisted surgical system, and/or by any other source as may serve a particular implementation. Image mode selector command 1210 may be received by image generator 1208 while visible light 120 and fluorescence excitation illumination 122 are concurrently being emitted and/or at any other suitable time.

To illustrate, image mode selector command 1210 may include a command to present a full-color image that does not include fluorescence image. In response to receiving this command, image generator 1208 may generate the full-color image based on the R, G, and B signals using any suitable image processing technique.

Alternatively, if image mode selector command 1210 includes a command to present a full-color fluorescence image, image generator 1208 may generate the full-color fluorescence image based on the R, G, B, and IR signals. This may be performed using any suitable image processing technique.

Figure 13:
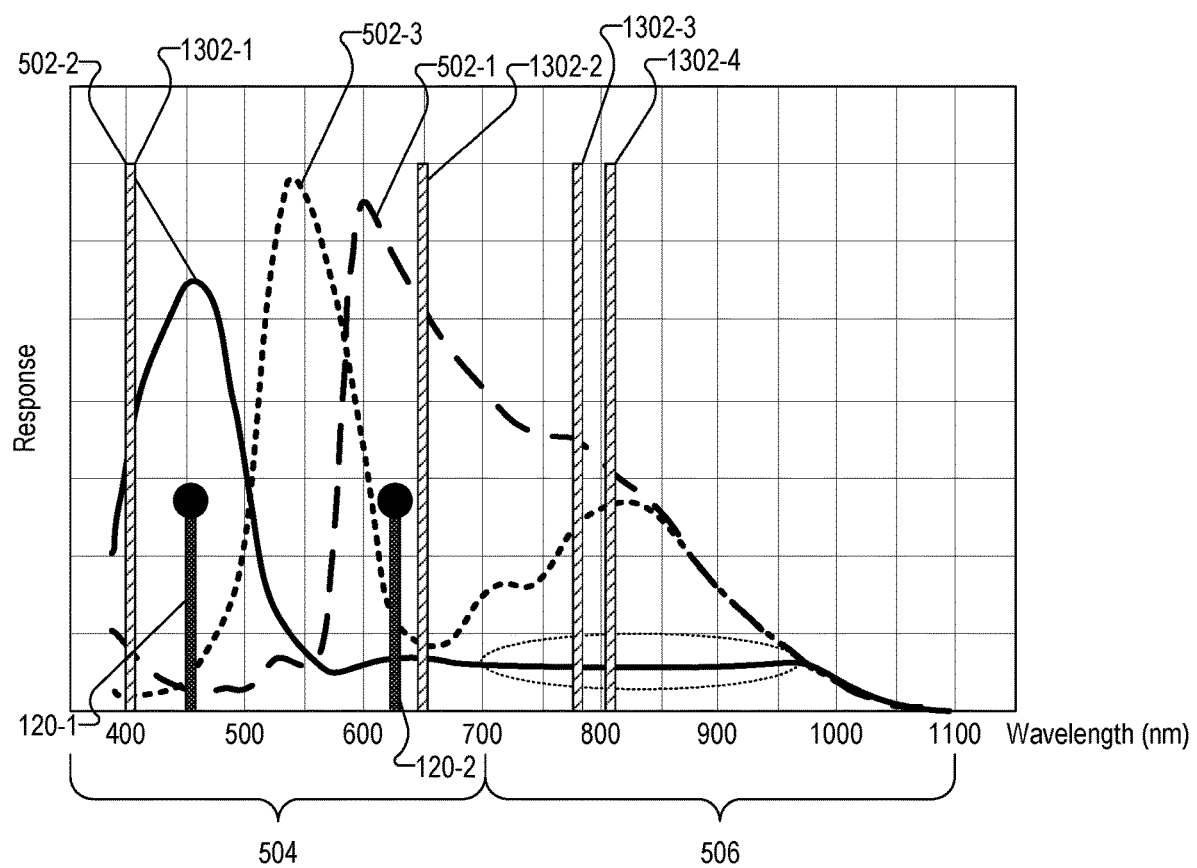
FIG. 13 shows narrowband cutoff filters superimposed on the spectral responses illustrated in FIG. 7 according to principles described herein.

FIG. 13 is similar to FIGS. 5 and 7, except that FIG. 13 also shows narrowband cutoff filters 1302-1 through 1302-4 superimposed on spectral responses 502. Narrowband cutoff filter 1302-1 is configured to filter out visible light having a wavelength of 405 nm, narrowband cutoff filter 1302-2 is configured to filter out visible light having a wavelength of 650 nm, narrowband cutoff filter 1302-3 is configured to filter out visible light having a wavelength of 785 nm, and narrowband cutoff filter 1302-4 is configured to filter out visible light having a wavelength of 803 nm.

Two or more of narrowband cutoff filters 1302 may be included in medical imaging system 100 depending on the particular wavelengths of fluorescence excitation illumination emitted by fluorescence excitation illumination system 118. For example, if fluorescence excitation illumination system 118 emits fluorescence excitation illumination having a wavelength of 405 nm and fluorescence excitation illumination having a wavelength of 803 nm, narrowband cutoff filters 1302-1 and 1302-4 may be included in medical imaging system 100.

FIG. 13 also shows a representation of visible light 120-1 and a representation visible light 120-2 emitted by visible light illumination system 116. As indicated by the positioning of the representations, visible light 120-1 is blue-biased and visible light 120-2 is red-biased in the example of FIG. 13.

FIG. 13 illustrates various benefits of the selectively configurable visible light illumination system 116 and fluorescence excitation illumination system 118. For example, if visible light illumination system 116 and fluorescence excitation illumination system 118 are both implemented by multiple illumination sources, illumination source control unit 130 may determine that a fluorescence imaging agent used in a patient fluoresces in response to fluorescence excitation illumination having a wavelength of 405 nm. Illumination source control unit 130 may accordingly activate one of the fluorescence excitation illumination sources that emits the 405 nm fluorescence excitation illumination. In this case, it is better to use the red-biased visible light 120-2 than the blue-biased visible light 120-1 as the visible light that also illuminates the scene. This is because narrowband cutoff filter 1302-1 would filter out some of blue-biased visible light 120-1 if blue-biased visible light 120-1 were to be used to illuminate the scene and because blue-biased visible light 120-1 could overwhelm the fluorescence illumination because of the relatively close proximity of the wavelengths of the blue-biased visible light 120-1 and the fluorescence illumination. Hence, in this example, illumination source control unit 130 may activate the visible light illumination source that emits visible light 120-2.

In contrast, illumination source control unit 130 may determine that a fluorescence imaging agent used in a patient fluoresces in response to fluorescence excitation illumination having a wavelength of 650 nm. Illumination source control unit 130 may accordingly activate one of fluorescence excitation illumination sources that emits the desired fluorescence excitation illumination. In this case, it is better to use the blue-biased visible light 120-1 than the red-biased visible light 120-2 as the visible light that also illuminates the scene. This is because narrowband cutoff filter 1302-2 would filter out some of red-biased visible light 120-2 if red-biased visible light 120-2 were to be used to illuminate the scene. Hence, in this example, illumination source control unit 130 may activate the visible light illumination source that emits visible light 120-1.

In cases where illumination source control unit 130 directs fluorescence excitation illumination system 118 to emit fluorescence excitation illumination in the infrared light range (e.g., 785 nm or 803 nm), illumination source control unit 130 may activate the visible light illumination source that emits blue-biased visible light 120-1 instead of the visible light illumination source that emits red-biased visible light 120-2 to illuminate the scene. This is due at least in part to the wavelength of blue-biased visible light 120-1 being further away from the wavelength of the fluorescence excitation illumination than the wavelength of red-biased visible light 120-2, which minimizes any chance that the visible light will be partially filtered by narrowband cutoff filters 1302-3 or 1302-4. Moreover, the visible light illumination source that emits visible light 120-1 may be selected in cases where the scene being imaged is a surgical area associated with a patient. In these cases, blue-biased visible light 120-1 may produce a sharper image than red-biased visible light 120-2 for reasons described in the co-pending application incorporated by reference herein.

Figure 14:
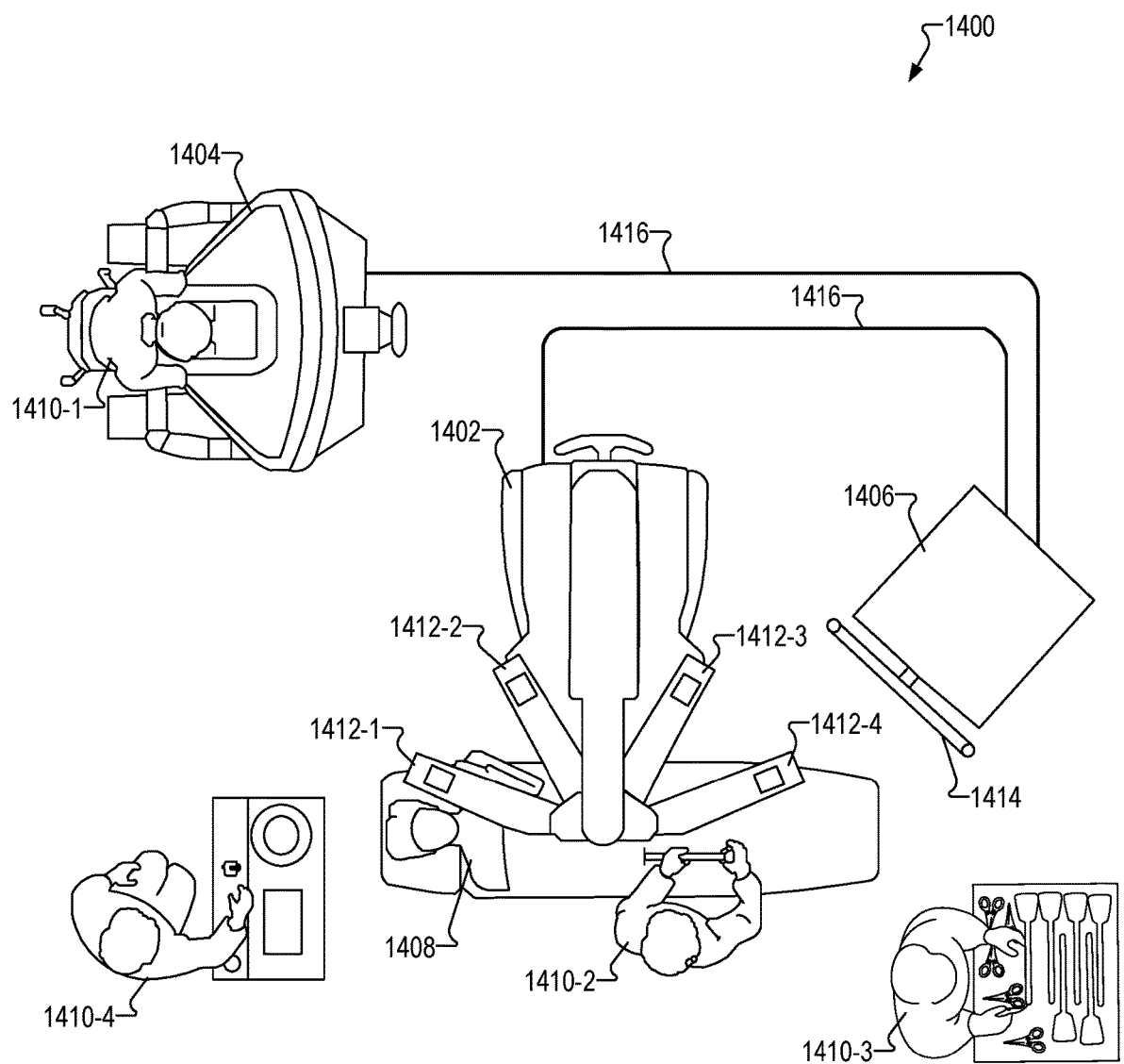
FIG. 14 illustrates an exemplary computer-assisted surgical system according to principles described herein.

FIG. 14 illustrates an exemplary computer-assisted surgical system 1400 ("surgical system 1400"). As shown, surgical system 1400 may include a manipulating system 1402, a user control system 1404, and an auxiliary system 1406 communicatively coupled one to another. Surgical system 1400 may be utilized by a surgical team to perform a computer-assisted surgical procedure on a patient 1408. As shown, the surgical team may include a surgeon 1410-1, an assistant 1410-2, a nurse 1410-3, and an anesthesiologist 1410-4, all of whom may be collectively referred to as "surgical team members 1410." Additional or alternative surgical team members may be present during a surgical session as may serve a particular implementation.

While FIG. 14 illustrates an ongoing minimally invasive surgical procedure, it will be understood that surgical system 1400 may similarly be used to perform open surgical procedures or other types of surgical procedures that may similarly benefit from the accuracy and convenience of surgical system 1400. Additionally, it will be understood that the surgical session throughout which surgical system 1400 may be employed may not only include an operative phase of a surgical procedure, as is illustrated in FIG. 14, but may also include preoperative, postoperative, and/or other suitable phases of the surgical procedure. A surgical procedure may include any procedure in which manual and/or instrumental techniques are used on a patient to investigate or treat a physical condition of the patient.

As shown in FIG. 14, manipulating system 1402 may include a plurality of manipulator arms 1412 (e.g., manipulator arms 1412-1 through 1412-4) to which a plurality of surgical instruments may be coupled. Each surgical instrument may be implemented by any suitable surgical tool (e.g., a tool having tissue-interaction functions), medical tool, imaging device (e.g., an endoscope), sensing instrument (e.g., a force-sensing surgical instrument), diagnostic instrument, or the like that may be used for a computer-assisted surgical procedure on patient 1408 (e.g., by being at least partially inserted into patient 1408 and manipulated to perform a computer-assisted surgical procedure on patient 1408). While manipulating system 1402 is depicted and described herein as including four manipulator arms 1412, it will be recognized that manipulating system 1402 may include only a single manipulator arm 1412 or any other number of manipulator arms as may serve a particular implementation.

Manipulator arms 1412 and/or surgical instruments attached to manipulator arms 1412 may include one or more displacement transducers, orientational sensors, and/or positional sensors used to generate raw (i.e., uncorrected) kinematics information. One or more components of surgical system 1400 may be configured to use the kinematics information to track (e.g., determine positions of) and/or control the surgical instruments.

User control system 1404 may be configured to facilitate control by surgeon 1410-1 of manipulator arms 1412 and surgical instruments attached to manipulator arms 1412. For example, surgeon 1410-1 may interact with user control system 1404 to remotely move or manipulate manipulator arms 1412 and the surgical instruments. To this end, user control system 1404 may provide surgeon 1410-1 with imagery (e.g., high-definition 3D imagery) of a surgical area associated with patient 1408 as captured by an imaging system (e.g., any of the medical imaging systems described herein). In certain examples, user control system 1404 may include a stereo viewer having two displays where stereoscopic images of a surgical area associated with patient 1408 and generated by a stereoscopic imaging system may be viewed by surgeon 1410-1. Surgeon 1410-1 may utilize the imagery to perform one or more procedures with one or more surgical instruments attached to manipulator arms 1412.

To facilitate control of surgical instruments, user control system 1404 may include a set of master controls. These master controls may be manipulated by surgeon 1410-1 to control movement of surgical instruments (e.g., by utilizing robotic and/or teleoperation technology). The master controls may be configured to detect a wide variety of hand, wrist, and finger movements by surgeon 1410-1. In this manner, surgeon 1410-1 may intuitively perform a procedure using one or more surgical instruments.

Auxiliary system 1406 may include one or more computing devices configured to perform primary processing operations of surgical system 1400. In such configurations, the one or more computing devices included in auxiliary system 1406 may control and/or coordinate operations performed by various other components (e.g., manipulating system 1402 and user control system 1404) of surgical system 1400. For example, a computing device included in user control system 1404 may transmit instructions to manipulating system 1402 by way of the one or more computing devices included in auxiliary system 1406. As another example, auxiliary system 1406 may receive, from manipulating system 1402, and process image data representative of imagery captured by an imaging device attached to one of manipulator arms 1412.

In some examples, auxiliary system 1406 may be configured to present visual content to surgical team members 1410 who may not have access to the images provided to surgeon 1410-1 at user control system 1404. To this end, auxiliary system 1406 may include a display monitor 1414 configured to display one or more user interfaces, such as images (e.g., 2D images) of the surgical area, information associated with patient 1408 and/or the surgical procedure, and/or any other visual content as may serve a particular implementation. For example, display monitor 1414 may display images of the surgical area together with additional content (e.g., graphical content, contextual information, etc.) concurrently displayed with the images. In some embodiments, display monitor 1414 is implemented by a touchscreen display with which surgical team members 1410 may interact (e.g., by way of touch gestures) to provide user input to surgical system 1400.

Manipulating system 1402, user control system 1404, and auxiliary system 1406 may be communicatively coupled one to another in any suitable manner. For example, as shown in FIG. 14, manipulating system 1402, user control system 1404, and auxiliary system 1406 may be communicatively coupled by way of control lines 1416, which may represent any wired or wireless communication link as may serve a particular implementation. To this end, manipulating system 1402, user control system 1404, and auxiliary system 1406 may each include one or more wired or wireless communication interfaces, such as one or more local area network interfaces, Wi-Fi network interfaces, cellular interfaces, etc.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 15:
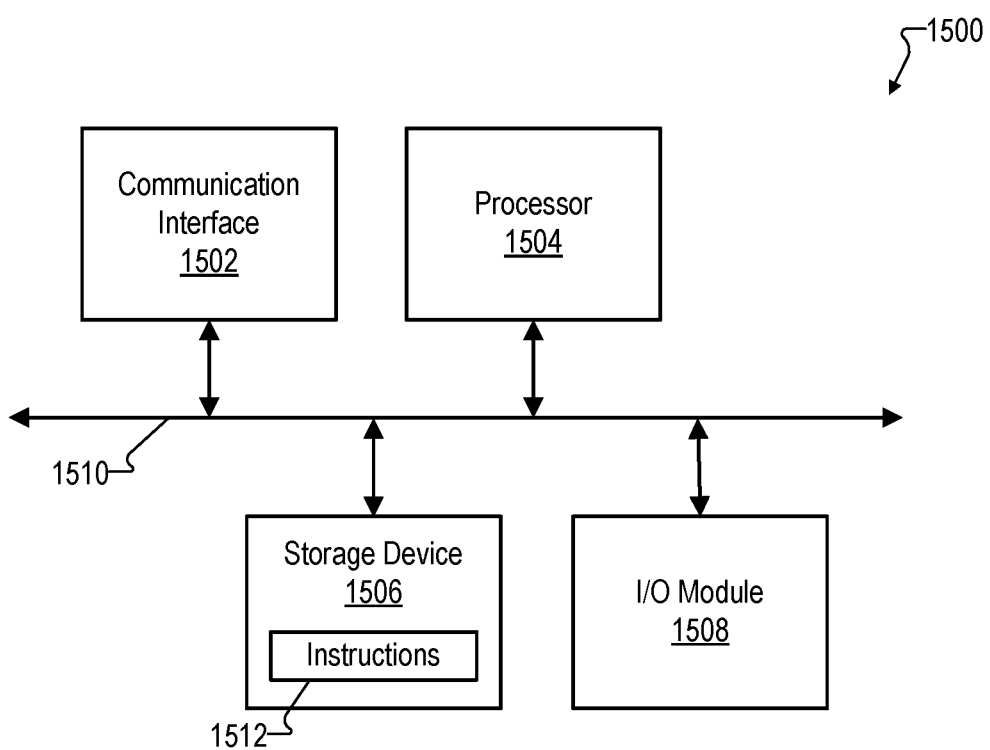
FIG. 15 illustrates an exemplary computing device according to principles described herein.

FIG. 15 illustrates an exemplary computing device 1500 that may be specifically configured to perform one or more of the processes described herein. Any of the systems, units, computing devices, and/or other components described herein may be implemented by computing device 1500.

As shown in FIG. 15, computing device 1500 may include a communication interface 1502, a processor 1504, a storage device 1506, and an input/output ("I/O") module 1508 communicatively connected one to another via a communication infrastructure 1510. While an exemplary computing device 1500 is shown in FIG. 15, the components illustrated in FIG. 15 are not intended to be limiting. Additional or alternative components may be used in other embodiments. Components of computing device 1500 shown in FIG. 15 will now be described in additional detail.

Communication interface 1502 may be configured to communicate with one or more computing devices. Examples of communication interface 1502 include, without limitation, a wired network interface (such as a network interface card), a wireless network interface (such as a wireless network interface card), a modem, an audio/video connection, and any other suitable interface.

Processor 1504 generally represents any type or form of processing unit capable of processing data and/or interpreting, executing, and/or directing execution of one or more of the instructions, processes, and/or operations described herein. Processor 1504 may perform operations by executing computer-executable instructions 1512 (e.g., an application, software, code, and/or other executable data instance) stored in storage device 1506.

Storage device 1506 may include one or more data storage media, devices, or configurations and may employ any type, form, and combination of data storage media and/or device. For example, storage device 1506 may include, but is not limited to, any combination of the non-volatile media and/or volatile media described herein. Electronic data, including data described herein, may be temporarily and/or permanently stored in storage device 1506. For example, data representative of computer-executable instructions 1512 configured to direct processor 1504 to perform any of the operations described herein may be stored within storage device 1506. In some examples, data may be arranged in one or more databases residing within storage device 1506.

I/O module 1508 may include one or more I/O modules configured to receive user input and provide user output. I/O module 1508 may include any hardware, firmware, software, or combination thereof supportive of input and output capabilities. For example, I/O module 1508 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1508 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1508 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A medical imaging system comprising:
   a visible light illumination system configured to selectively emit one of
      a first visible light biased to a first wavelength associated with a first color, and
      a second visible light biased to a second wavelength associated with a second color;
   a fluorescence excitation illumination system comprising:
      a first fluorescence excitation illumination source configured to emit a first fluorescence excitation illumination having a third wavelength to elicit fluorescence illumination by a first fluorescence imaging agent, the third wavelength closer to the first wavelength than to the second wavelength, and
      a second fluorescence excitation illumination source configured to emit a second fluorescence excitation illumination having a fourth wavelength to elicit fluorescence illumination by a second fluorescence imaging agent, the fourth wavelength closer to the second wavelength than to the first wavelength; and
   an illumination source control unit communicatively coupled to the visible light illumination system and the fluorescence excitation illumination system, the illumination source control unit configured to:
      identify, based on a wavelength of fluorescence illumination that is emitted when a particular fluorescence excitation illumination is applied within a patient while a particular fluorescence imaging agent is used in the patient, the particular fluorescence imaging agent as being either the first fluorescence imaging agent or the second fluorescence imaging agent
      selectively direct, when the illumination source control unit identifies the particular fluorescence imaging agent used in the patient as being the first fluorescence imaging agent, the visible light illumination system to emit the second visible light and the fluorescence excitation illumination system to emit the first fluorescence excitation illumination concurrently with the emission of the second visible light for use with the first fluorescence imaging agent, the selective directing of the fluorescence excitation illumination system to emit the first fluorescence excitation illumination comprising activating the first fluorescence excitation illumination source and deactivating the second fluorescence excitation illumination source, and
      selectively direct, when the illumination source control unit identifies the particular fluorescence imaging agent used in the patient as being the second fluorescence imaging agent, the visible light illumination system to emit the first visible light and the fluorescence excitation illumination system to emit the second fluorescence excitation illumination concurrently with the emission of the first visible light for use with the second fluorescence imaging agent, the selective directing of the fluorescence excitation illumination system to emit the second fluorescence excitation illumination comprising activating the second fluorescence excitation illumination source and deactivating the first fluorescence excitation illumination source.

2. The medical imaging system of claim 1, further comprising:
   an image sensor comprising a two by two array of pixels that includes a first pixel, a second pixel, a third pixel, and a fourth pixel;
   a first color filter that covers the first pixel and that is configured to allow the first pixel to collect a first visible light color component of the first and second visible light and prevent the first pixel from collecting second and third visible light color components of the first and second visible light;
   a second color filter that covers the second pixel and the third pixel, the second color filter configured to allow the second and third pixels to each collect the second visible light color component and prevent the second and third pixels from each collecting the first and third visible light color components; and
   a third color filter that covers the fourth pixel and that is configured to allow the fourth pixel to collect the third visible light color component and prevent the fourth pixel from collecting the first and second visible light color components.

3. The medical imaging system of claim 2, wherein:
   the first visible light color component is a red component;
   the second visible light component is a blue component; and
   the third visible light component is a green component.

4. The medical imaging system of claim 2, wherein:
   the first visible light color component is a red component;
   the second visible light component is a green component; and
   the third visible light component is a blue component.

5. The medical imaging system of claim 2, further comprising a pixel- level broadband infrared cutoff filter that covers the second pixel and that is configured to prevent the second pixel from collecting infrared light.

6. The medical imaging system of claim 5, wherein the pixel-level broadband infrared cutoff filter comprises a coating configured to adhere to a surface of the second pixel.

7. The medical imaging system of claim 5, wherein the first, third, and fourth pixels are not covered by pixel-level broadband infrared cutoff filters configured to prevent the first, third, and fourth pixels from collecting the infrared light.

8. The medical imaging system of claim 7, further comprising a narrowband cutoff filter that covers the first, third, and fourth pixels and that is configured to prevent the first, third, and fourth pixels from collecting at least one of the first fluorescence excitation illumination and the second fluorescence excitation illumination.

9. The medical imaging system of claim 8, wherein the narrowband cutoff filter comprises a glass filter that covers the first, second, third, and fourth pixels.

10. The medical imaging system of claim 8, wherein the narrowband cutoff filter comprises:
- a first pixel-level narrowband cutoff filter that covers the first pixel;
- a second pixel-level narrowband cutoff filter that covers the third pixel; and
- a third pixel-level narrowband cutoff filter that covers the fourth pixel.

11. The medical imaging system of claim 1, wherein:
the third wavelength is in a visible light range; and
the fourth wavelength is in an infrared light range.

12. The medical imaging system of claim 1, wherein:
the visible light illumination system comprises
- a first visible light illumination source configured to emit the first visible light, and
- a second visible light illumination source configured to emit the second visible light;

the selective directing of the visible light illumination system to emit the first visible light comprises selectively activating the first visible light illumination source; and the selective directing of the visible light illumination system to emit the second visible light comprises selectively activating the second visible light illumination source.

13. The medical imaging system of claim 1, wherein:

the visible light illumination system comprises a single adjustable visible light illumination source;

the selective directing of the visible light illumination system to emit the first visible light comprises adjusting the single adjustable visible light illumination source to selectively emit the first visible light; and the selective directing of the visible light illumination system to emit the second visible light comprises adjusting the single adjustable visible light illumination source to selectively emit the second visible light.

* * * * *